US006083977A

United States Patent [19]
Boehm et al.

[11] Patent Number: 6,083,977
[45] Date of Patent: Jul. 4, 2000

[54] TRIENOIC RETINOID COMPOUNDS AND METHODS

[75] Inventors: Marcus F. Boehm; Lin Zhang; Alex M. Nadzan, all of San Diego, Calif.

[73] Assignee: Ligand Pharmaceuticals Incorporated, San Diego, Calif.

[21] Appl. No.: 08/481,877

[22] Filed: Jun. 7, 1995

Related U.S. Application Data

[63] Continuation-in-part of application No. 08/366,613, Dec. 30, 1994, abandoned.
[51] Int. Cl.[7] .......................... A61K 31/35; C07D 311/74; C07D 311/76
[52] U.S. Cl. ..................... 514/457; 514/912; 549/401; 549/403
[58] Field of Search ...................... 549/401, 403; 514/457, 912

[56] References Cited

U.S. PATENT DOCUMENTS

| | | | |
|---|---|---|---|
| 4,472,430 | 9/1984 | Loev et al. | 424/312 |
| 4,534,979 | 8/1985 | Loev et al. | 514/329 |
| 4,648,996 | 3/1987 | Aig et al. | 514/544 |
| 4,894,480 | 1/1990 | Aig et al. | 568/11 |
| 5,320,833 | 6/1994 | Deckers et al. | 514/938 |
| 5,705,167 | 1/1998 | Bernardon et al. | 424/401 |

FOREIGN PATENT DOCUMENTS

4036779A1  11/1990  Germany.

OTHER PUBLICATIONS

Chem Abst. vol. 75 No. 48 745, Badr et al "Resuable navigator of allyl aromatics" 1971.

Aurell, M., et al., "Trienediolates of Hexadienoic Acids in Synthesis. Synthesis of Retinoic and nor–Retinoic Acids." *Tetrahedron*, vol. 49, 27:6089–6100 (1993).

Boehm, M., et al., "Synthesis of High Specific Activity [$^3$H]–cis–Retinoic Acid and Its Application for Identifying Retinoids with Unusual Binding Properties," *Journal of Medicinal Chemistry*, vol. 37, 3:408–414 (1994).

Boehm, M., et al., "Synthesis and Structure—Activity Relationships of Novel Retinoid X Receptor–Selective Retinoids," *Journal of Medicinal Chemistry*, vol. 37, 18:2930–2941 (1994).

Liu, R., et al., "Photochemistry and Synthesis of Stereoisomers of Vitamin A," *Tetrahedron*, vol. 40, 11:1931–1969 (1984).

Kagechika, H., et al., "Retinobenzoic Acids. 4. Conformation of Aromatic Amides with Retinoidal Activity. Importance of trans–Amide Structure for the Activity," *Journal of Medicinal Chemistry*, vol. 32, 2292–2296 (1989).

Kagechika, H., et al., "Retinobenzoic Acids. 3. Structure–Activity Relationships of Retinoidal Azobenzene–4–carboxylic Acids and Stilbene–4–carboxylic Acids," *Journal of Medicinal Chemistry*, vol. 32, 1098–1108 (1989).

Kagechika, H., et al., "Retinobenzoic Acids. 2. Structure–Activity Relationships of Chalcome–4–carboxylic Acids and Flavone–4'–carboxylic Acids," *Journal or Medicinal Chemistry*, vol. 32, 834–840 (1989).

*Primary Examiner*—John Kight
*Assistant Examiner*—Raymond Covington
*Attorney, Agent, or Firm*—J. Scott Elmer; William L. Respess

[57] ABSTRACT

Novel trienoic retinoid compounds having activity for retinoic acid receptors and retinoid X receptors are provided. Also provided are pharmaceutical compositions incorporating such compounds and methods for their use.

37 Claims, No Drawings

TRIENOIC RETINOID COMPOUNDS AND METHODS

CROSS REFERENCE TO RELATED APPLICATIONS

This Application is a Continuation-In-Part Application of pending U.S. patent application Ser. No. 08/366,613, filed Dec. 30, 1994, the entire disclosure of which is herein incorporated by reference.

FIELD OF THE INVENTION

The present invention relates to compounds having activity for retinoic acid receptors and retinoid X receptors, and to methods for the therapeutic use of such compounds.

BACKGROUND OF THE INVENTION

The vitamin A metabolite, retinoic acid, has long been recognized to induce a broad spectrum of biological effects. In addition, a variety of structural analogues of retinoic acid have been synthesized that also have been found to be bioactive. Some, such as Retin-A® and Accutane®, have found utility as therapeutic agents for the treatment of various pathological conditions. In addition, synthetic retinoids have been found to mimic many of the pharmacological actions of retinoic acid.

Medical professionals have become very interested in the therapeutic applications of retinoids. Among their uses approved by the FDA is the treatment of severe forms of acne and psoriasis. A large body of evidence also exists that these compounds can be used to arrest and, to an extent, reverse the effects of skin damage arising from prolonged exposure to the sun. Other evidence exists that these compounds may be useful in the treatment and prevention of a variety of cancerous and pre-cancerous conditions, such as melanoma, cervical cancer, some forms of leukemia, oral leukoplakia and basal and squamous cell carcinomas. Retinoids have also shown an ability to be efficacious in treating and preventing diseases of the eye, cardiovascular system, immune system, skin, respiratory and digestive tracts, and as agents to facilitate wound healing and modulate programmed cell death (apoptosis).

Major insight into the molecular mechanism of retinoic acid signal transduction was gained in 1988, when a member of the steroid/thyroid hormone intracellular receptor superfamily was shown to transduce a retinoic acid signal. Evans, *Science*, 240:889–95 (1988); Giguere et al., *Nature*, 330:624–29 (1987); Petkovich et al., *Nature*, 330: 444–50 (1987). It is now known that retinoids regulate the activity of two distinct intracellular receptor subfamilies; the Retinoic Acid Receptors (RARs) and the Retinoid X Receptors (RXRs), including their isoforms, RARα, β, γ and RXRα, β, γ. In this regard, an endogenous low-molecular-weight ligand which modulates the transcriptional activity of the RARs is all-trans-retinoic acid (ATRA), while an endogenous ligand for the RXRs is 9-cis retinoic acid (9-cis). Heyman et al., *Cell*, 68:397–406 (1992) and Levin et al. *Nature*, 355:359–61 (1992).

Although both the RARs and RXRs respond to ATRA in vivo, due to the in vivo conversion of some of the ATRA to 9-cis, the receptors differ in several important aspects. First, the RARs and RXRs are significantly divergent in primary structure (e.g., the ligand binding domains of RARE and RXRα have only 27% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, in contrast to the RARs, which are not expressed at high levels in the visceral tissues, RXRα mRNA has been shown to be most abundant in the liver, kidney, lung, muscle and intestine. Finally, the RARs and RXRs have different target gene specificity. For example, response elements have recently been identified in the cellular retinal binding protein type II (CRBPII) and Apolipoprotein AI genes which confer responsiveness to RXR, but not RAR. Furthermore, RAR has also been recently shown to repress RXR-mediated activation through the CRBPII RXR response element (Manglesdorf et al., *Cell*, 66:555–61 (1991)). These data indicate that two retinoic acid responsive pathways are not simply redundant, but instead manifest a complex interplay.

In view of the related, but clearly distinct, nature of these receptors, retinoids which are more selective for the RAR subfamily or the RXR subfamily would be of great value for selectively controlling processes mediated by one or more of the RAR or RXR isoforms, and would provide the capacity for independent control of the physiologic processes mediated by the RARs or RXRs. In addition, pan-agonist retinoids that activate one or more isoforms of both the RARs and RXRs would also be valuable for controlling processes mediated by both of these subfamilies of retinoid receptors. Furthermore, retinoids which preferentially affect one or more but not all of the receptor isoforms also offer the possibility of increased therapeutic efficacy and reduced side effect profiles when used for therapeutic applications.

Various polyene compounds have been disclosed to be useful in the treatment of inflammatory conditions, psoriasis, allergic reactions, and for use in sunscreens in cosmetic preparations. See e.g., U.S. Pat. Nos. 4,534,979 and 5,320,833. In addition, trienediolates of hexadienoic acids have proved useful in the synthesis of retinoic and nor-retinoic acids. See M. J. Aurell, et al., 49 *Tetrahedron*, 6089 (1993). However, no retinoid activity has been ascribed to these compounds.

SUMMARY OF THE INVENTION

The present invention provides novel trienoic compounds that have selective activity on RARs and RXRs or pan-agonist activity on one or more each of the RAR and RXR isoforms. The present invention also provides labeled retinoid compounds, pharmaceutical compositions incorporating these novel trienoic compounds and methods for the therapeutic use of such compounds and pharmaceutical compositions.

These and various other advantages and features of novelty which characterize the invention are pointed out with particularity in the claims annexed hereto and forming a part hereof. However, for a better understanding of the invention, its advantages, and objects obtained by its use, reference should be had to the accompanying descriptive matter, in which there is illustrated and described preferred embodiments of the invention.

Definitions

In accordance with the present invention and as used herein, the following terms are defined with the following meanings, unless explicitly stated otherwise.

The term alkyl refers to straight-chain, branched-chain or cyclic structures that are optionally saturated or unsaturated (thereby resulting in alkenyl and alkynyl structures), as well as combinations thereof.

The term aryl refers to an optionally substituted six-membered aromatic ring.

The term heteroaryl refers to an optionally substituted five-membered or six-membered heterocyclic ring containing one or more heteroatoms selected from the group consisting of oxygen, nitrogen and sulfur.

The terms retinoid or retinoids refer to compound(s) that bind and/or activate one or more retinoid receptors, thereby affecting the transcriptional activity of a target gene to which the activated receptor and compound complex binds.

The term pan-agonist refers to a retinoid that activates at least one member of both the RAR subfamily (i.e., RARα, RARβ, or RARγ) and the RXR subfamily (i.e., RXRα, RXRβ, or RXRγ). Preferably such pan-agonist retinoids activate all members of both the RAR and RXR subfamilies of retinoid receptors.

As used herein, isotopic labels or radiolabels refer to substituents labeled with deuterium, tritium, carbon 13 and/or carbon 14, including, but not limited to $^{14}CH_3$, $^{13}CH_3$, $CD_3$, $C^3H_3$, and $^{13}CD_3$.

DETAILED DESCRIPTION OF EMBODIMENTS OF THE INVENTION

In accordance with a first aspect of the present invention, we have developed novel trienoic compounds having the formulae:

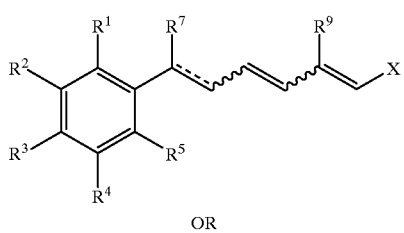

(I)

OR

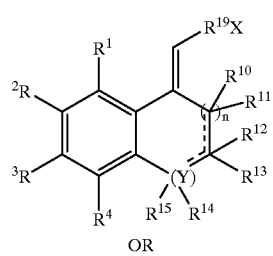

(II)

OR

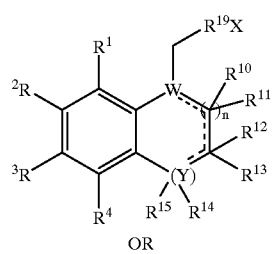

(III)

OR

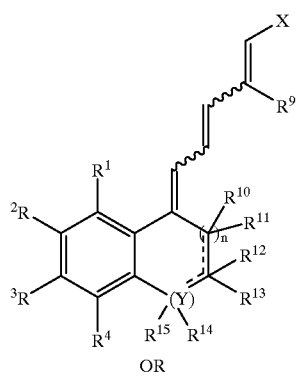

(IV)

OR

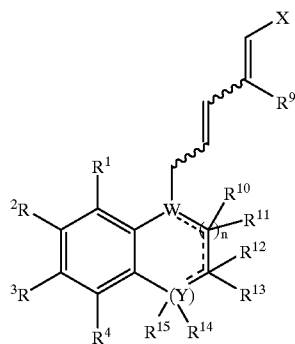

(V)

wherein:

$R^1$, $R^2$ and $R^4$ each independently are hydrogen, aryl, heteroaryl, $CF_3$ or a $C_2$–$C_6$ alkyl, fluoroalkyl or perfluoroalkyl optionally substituted with $^{14}CH_3$, $^{13}CH_3$, $CD_3$, $C^3H_3$, and/or $^{13}CD_3$;

$R^3$ and $R^5$ each independently are hydrogen, $CF_3$, a $C_1$–$C_3$ alkyl, a $C_1$ to $C_3$ fluoroalkyl or perfluoroalkyl, or $OR^6$, where $R^6$ is hydrogen, $CF_3$, a $C_1$–$C_2$ alkyl or a $C_1$ to $C_2$ fluoroalkyl or perfluoroalkyl, provided, however, that $R^1$ and $R^5$ cannot be $CF_3$ or alkyl, fluoroalkyl or perfluoroalkyl when $R^3$ is $CF_3$ or alkyl, fluoroalkyl or perfluoroalkyl;

$R^7$ is a $C_1$–$C_4$ alkyl optionally substituted with $^{14}CH_3$, $^{13}CH_3$, $CD_3$, $C^3H_3$, and/or $^{13}CD_3$ or $CH_2OR^8$, where $R^8$ represents hydrogen, a $C_1$–$C_6$ alkyl, a $C_3$–$C_7$ saturated or unsaturated cycloalkyl optionally substituted with a $C_1$–$C_4$ alkyl, F, Cl, Br, I, OH, $CF_3$, $OR^6$, $NR^6$, where $R^6$ has the definition given above;

$R^9$ is a $C_1$–$C_4$ alkyl;

$R^{10}$ through $R^{15}$ each independently are hydrogen, a $C_1$–$C_6$ alkyl or $CF_3$;

X is $COOR^{16}$, $CONR^{17}$, or $CONHR^{17}R^{18}$ where $R^{16}$ represents hydrogen or a $C_1$–$C_6$ alkyl, and where $R^{17}$ and $R^{18}$ each independently represent a $C_1$–$C_6$ alkyl, or an aryl or heteroaryl optionally substituted with OH, F, Br, Cl or I, provided, however, that $R^{17}$ and $R^{18}$ both cannot be an aryl or heteroaryl;

Y is C, O, S or N, provided that, when Y is O, then $R^{14}$ and $R^{15}$ do not exist, and when Y is N, then $R^{14}$ and $R^{15}$ cannot be $CF_3$, and when Y is S, then R and R can independently or together represent O, or may be absent altogether;

W is N or $CR^{16}$, where $R^{16}$ has the same definition given above;

$R^{19}$ is an aryl or heteroaryl optionally substituted with one or more substituents selected from the group consisting of hydrogen, F, Cl, Br, I or a $C_1$–$C_6$ alkyl, wherein X has the same definition given above;

n is 0, 1 or 2;

the dotted lines designate optional double bonds; and the wavy lines depict carbon to carbon bonds in either the cis or trans configurations, provided, however, that when $R^1$, $R^2$, $R^4$ and $R^5$ are all hydrogen, then $R^3$ cannot be aryl.

Preferably, $R^1$, $R^2$ and $R^4$ independently represent $C_3$–$C_6$ branched alkyls, fluoroalkyls or perfluoroalkyls, more preferably $R^2$ and $R^4$ independently represent $C_3$–$C_6$ branched alkyls, fluoroalkyls or perfluoroalkyls, while $R^1$, $R^3$ and $R^5$ are all hydrogen, and most preferably $R^2$ and $R^4$ are selected from the group consisting of isopropyl, t-butyl and $CF_3$, while $R^1$, $R^3$ and $R^5$ are all hydrogen.

The compounds of the present invention also include all pharmaceutically acceptable salts, as well as esters, amides and prodrugs. Preferably, such salts, esters and amides, will be formed at the $R^{16}$, $R^{17}$ and/or $R^{18}$ positions. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl) aminomethane. Additional pharmaceutically acceptable salts are known to those skilled in the art.

The compounds of the present invention exhibit retinoid activity and are particularly useful in the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin pigmentation agents and to treat and reverse the effects of age and photo damage to the skin. The compounds are also useful for the prevention and treatment of cancerous and pre-cancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposis sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of restenosis and as an agent to increase the level of circulating tissue plasminogen activator (TPA). Other uses for the compounds of the present invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and Amyotrophic Lateral Sclerosis (ALS), improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. It will also be understood by those skilled in the art that the retinoid compounds of the present invention will prove useful in any therapy in which retinoids, including RAR selective retinoids, RXR selective retinoids, and pan-agonist retinoids will find application.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative compounds of the present invention include, without limitation, ethyl (2E, 4E, 6E)-7-(3,5-di-t-butylphenyl)-3-methylocta-2,4,6-trienoate; ethyl (2E, 4E, 6Z)-7-(3,5-di-t-butylphenyl)-3-methylocta-2,4,6-trienoate; (2E, 4E, 6E)-7-(3,5-di-t-butylphenyl)-3-methylocta-2,4,6-trienoic acid; (2E, 4E, 6Z)-7-(3,5-di-t-butylphenyl)-3-methylocta-2,4,6-trienoic acid; ethyl (2E, 4E)-7-(3,5-di-t-butylphenyl)-3-methylocta-2,4-dienoate; (2E, 4E)-7-(3,5-di-t-butylphenyl)-3-methylocta-2,4-dienoic acid; ethyl (2E, 4E, 6E)-7-(3,5-di-t-butylphenyl)-3-methyldeca-2,4,6-trienoate; ethyl (2E, 4E, 6E)-7-(3,5-di-t-butylphenyl)-3-methyldeca-2,4,6-trienoate; (2E, 4E, 6E)-7-(3,5-di-t-butylphenyl)-3-methyldeca-2,4,6-trienoic acid; (2E, 4E, 6Z)-7-(3,5-di-t-butylphenyl)-3-methyldeca-2,4,6-trienoic acid; ethyl (2E,4E,6E)-6-(6,8-di-t-butylchroman-4-ylidene)-3-methylhexa-2,4,6-trienoate; ethyl (2E,4E,6Z)-6-(6,8-di-t-butylchroman-4-ylidene)-3-methylhexa-2,4,6-trienoate; (2E,4E,6E)-6-(6,8-di-t-butylchroman-4-ylidene)-3-methylhexa-2,4,6-trienoic acid; (2E,4E,6Z)-6-(6,8-di-t-butylchroman-4-ylidene)-3-methylhexa-2,4,6-trienoic acid; (2E, 4E, 6E)-7-(3,5-di-trifluoromethylphenyl)-3-methylocta-2,4,6-trienoic acid; (2E, 4E, 6Z)-7-(3,5-di-trifluoromethylphenyl)-3-methylocta-2,4,6-trienoic acid; (2E, 4E, 6E)-7-(3,5-di-isopropylphenyl)-3-methylocta-2,4,6-trienoic acid; (2E, 4E, 6Z)-7-(3,5-di-isopropylphenyl)-3-methylocta-2,4,6-trienoic acid; (2E, 4E, 6E)-7-(4-t-butylphenyl)-3-methylocta-2,4,6-trienoic acid; (2E, 4E, 6E)-7-(3,5-di-t-butyl-4-methoxyphenyl)-3-methylocta-2,4,6-trienoic acid; (2E, 4E, 6E)-3-methyl-7-(3,5-di-t-butyl-4-methoxyphenyl)octa-2,4,6-trienoic acid; (2E,4E,6E)-3-methyl-7-(3,4-diethylphenyl)octa-2,4,6-trienoic acid; (2E, 4E,6Z)-3-methyl-7-(3,4-di-ethylphenyl)octa-2,4,6-trienoic acid; (2E, 4E, 6E)-3-methyl-7-(3,5-di-t-butyl-4-ethoxyphenyl)octa-2,4,6-trienoic acid; (2E,4E,6E)-3-methyl-7-(3,4-di-t-butylphenyl)octa-2,4,6-trienoic acid; (2E,4E,6E)-3-methyl-7-cyclohexyl-7-(3,5-di-t-butylphenyl) hepta-2,4,6-trienoic acid; (2E,4E,6E)-3-methyl-7-(3,5-di-t-butylphenyl)nona-2,4,6-trienoic acid; and (2E,4E,6Z)-3-methyl-7-(3,4-diethyl-6-methylphenyl)nona-2,4,6-trienoic acid.

The compounds of the present invention can be obtained by routine chemical synthesis by those skilled in the art, e.g., by modification of the compounds disclosed or by a total synthesis approach. In this regard, the synthesis of the compounds of the present invention follows well established retinoid synthesis schemes and techniques as described in M. I. Dawson and W. H. Okamura, "Chemistry and Biology of Synthetic Retinoids", Chapters 3, 8, 14 and 16, CRC Press, Inc., Florida (1990); M. I. Dawson and P. D. Hobbs, *The Synthetic Chemistry of Retinoids,* In Chapter 2: "The Retinoids, Biology, Chemistry and Medicine", M. B. Sporn et al., Eds. (2nd ed.), Raven Press, New York, New York, pp. 5–178 (1994) and R. S. H. Liu and A. E. Asato, "Photochemistry and Synthesis of Stereoisomers of Vitamin A," 40 *Tetrahedron,* 1931 (1984), the disclosures of which are herein incorporated by reference. The sequence of steps of the general methods of synthesizing the compounds of the present invention are shown below. In addition, more detailed and illustrative synthetic schemes for specific compounds of the present invention will be found in the Examples included herein.

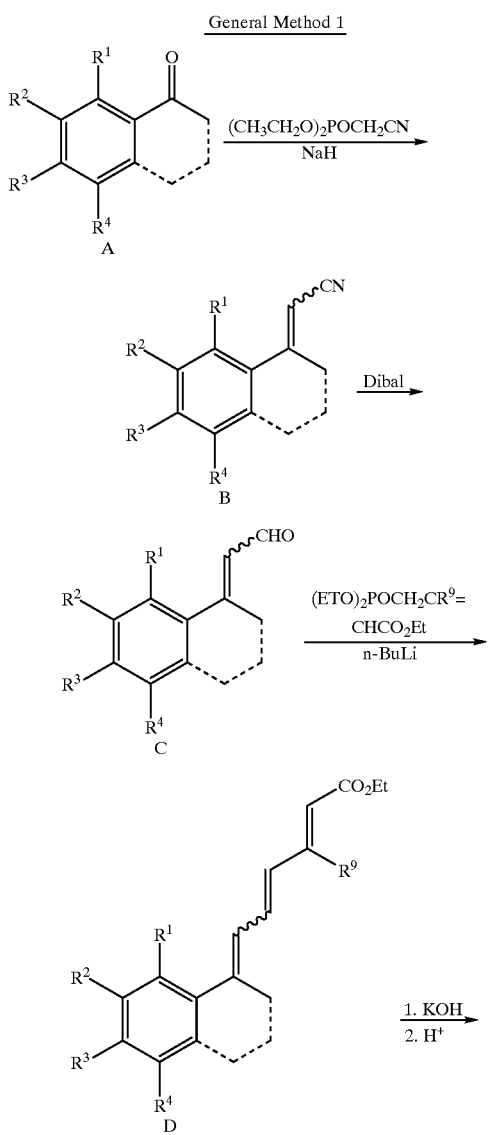

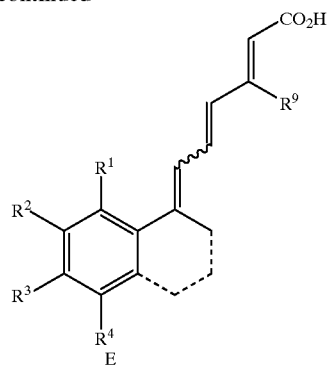

In General Method 1, the compounds of the present invention may be prepared by treatment of an aryl ketone A with a phosphonate, such as diethylcyanomethylphosphonate, to give the nitrile B, followed by reduction of B (where the optional single or double bonds are illustrated with dashed lines) in the presence of a reducing agent, such as diisobutyl aluminum hydride (Dibal) to provide the aldehyde C. The cis and trans isomers of aldehyde C may be separated at this stage via thin-layer chromatography (TLC), or other recognized procedures known to those skilled in the art. These separated aldehydes C are then treated with a phosphonate, such as triethyl-3-alkyl-4-phosphonocrotonate, to give the trienoate esters D, which in turn can be saponified under basic conditions to give the carboxylic acid E.

Alternatively, utilizing General Method 2, shown below, the cis isomer of aldehyde C may be prepared from the alkyne F. Specifically, aryl alkyne F is prepared from aryl acetophenone A by treatment with a phosphorylating agent, such as ClPO(EtO)$_2$, in the presence of a strong base, such as lithium diisopropylamide (LDA). Aryl alkyne F is then treated with a suitable nitrile source, such as PhOCN, in the presence of base, such as nBuLi, to give nitrile G, which is then subjected to reductive methylation to give exclusively the cis isomer of nitrile B. Nitrile B is then reduced to the corresponding aldehyde C and homologated in the same fashion as described in General Method 1 above to yield compounds D and E.

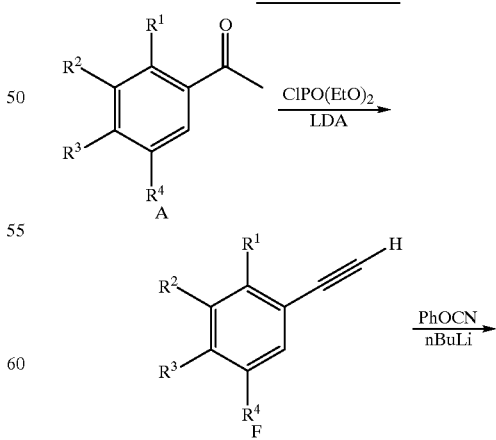

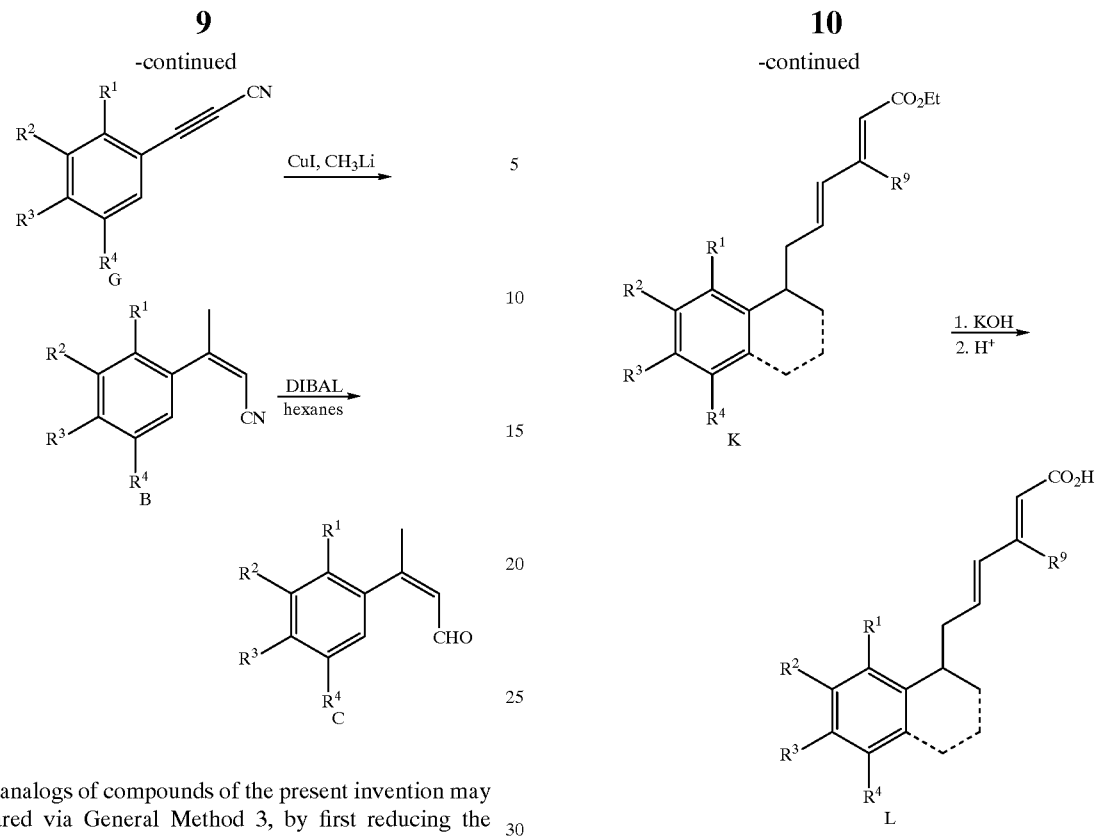

Other analogs of compounds of the present invention may be prepared via General Method 3, by first reducing the double bond of nitrile B (where the single or double optional bonds are illustrated with dashed lines) to give nitrile I. Thereafter nitrile I is reduced in the presence of Dibal to yield aldehyde J, which in turn is treated with a phosphonate, such as triethyl-3-alkyl-4-phosphonocrotonate, to give dienoate ester K. Saponification of dienoate ester K via base, such as KOH/MeOH, gives the dienoic acid L.

General Method 3

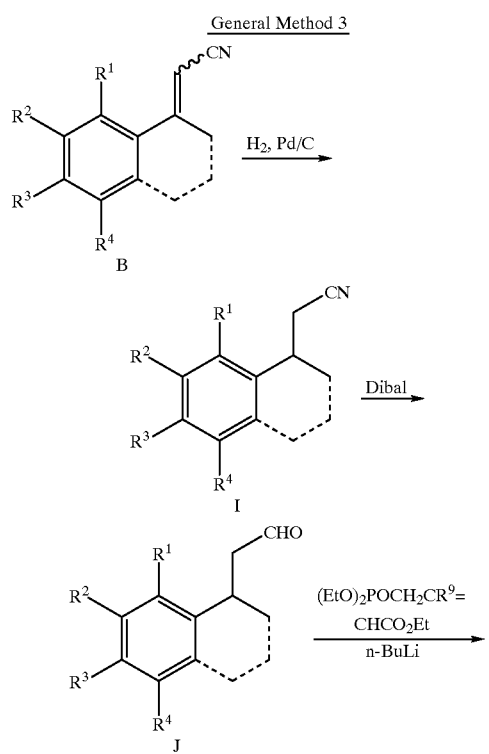

Radiolabeled homologs of the compounds of the present invention may be prepared by the General Method 4 shown below. Specifically, compound A is oxidized to methyl ester B which is then reduced with a tritium hydride source, such as LiAl$^3$H$_4$, to alcohol C. Oxidation of the tritiated alcohol C to aldehyde D, followed by condensation with the ylide of triethylphosphonocrotonate gives the tritiated ester E. Ester E may then be saponified to give the final tritium labeled acid F in high yield with high (>20 Ci/mmol) specific activity. This methodology is described in detail in Boehm et al., "Synthesis of High Specific Activity [$^3$H]-9-cis-Retinoic Acid and Its Application for Identifying Retinoids with Unusual Binding Properties", 37 *J. Med. Chem.*, 408–414 (1994), the disclosure of which is herein incorporated by reference.

General Method 4:
Preparation of Radiolabeled Homologs

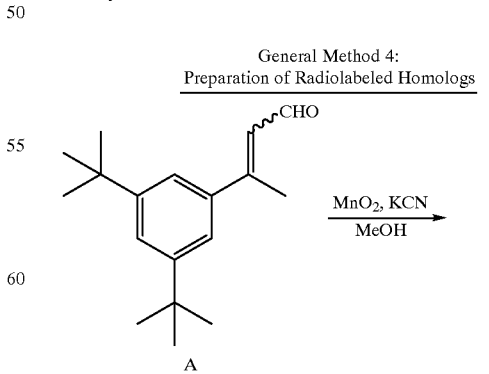

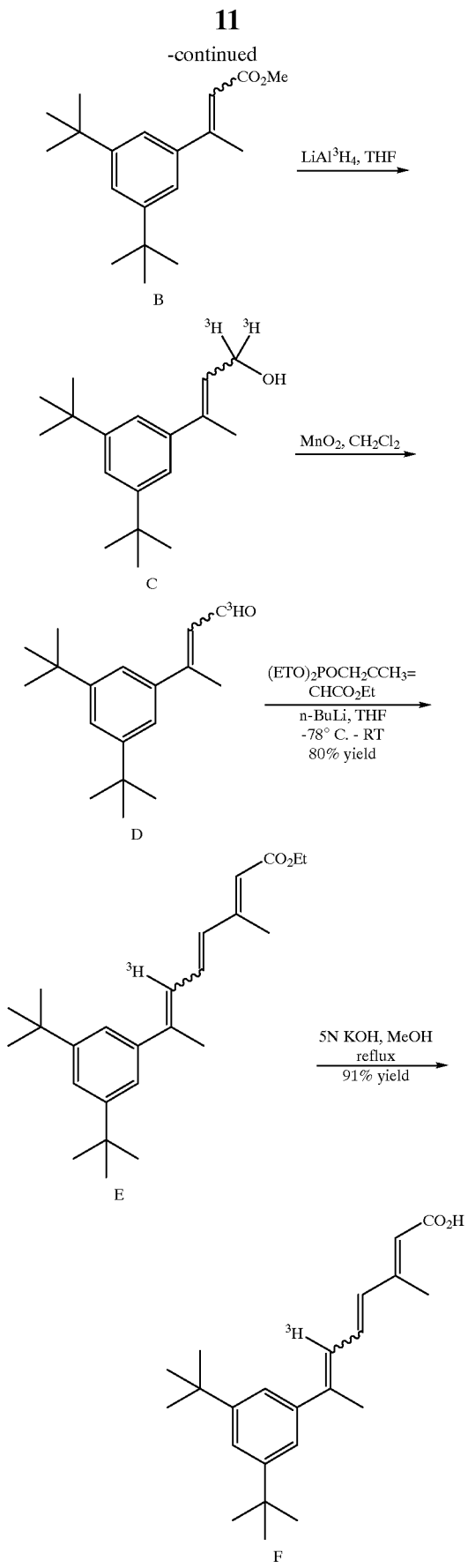

It will be understood by those skilled in the art that certain modifications can be made to the above-described methods that remain within the scope of the present invention. For example, the compounds of the present invention may also be produced in the form of the corresponding amides or esters, appropriate phosphoranes may be substituted for phosphonates, and reducing agents other than LiAl$^3$H$_4$ may be utilized in the syntheses outlined above. Furthermore, it will be understood that other isotopic labels may be employed, including $^{13}$CH$_3$, $^{13}$CD$_3$ and the like.

These labels may be introduced using the appropriate labeled MeLi (e.g., $^{13}$CH$_3$Li) as shown in Scheme 1. Thereafter, the remainder of the synthesis is as shown in Scheme 1.

In another aspect, the retinoid compounds, their pharmaceutically acceptable salts or hydrolyzable esters of the present invention are combined in a mixture with a pharmaceutically acceptable carrier to provide pharmaceutical compositions useful for treating the biological conditions or disorders noted herein in mammalian species, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose CreaMTM™ (Johnson & Johnson) hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when labeled and used in assays to determine the presence of RARs and RXRs. They are particularly useful due to their ability to selectively bind to members of the RAR and RXR subfamilies and can therefore be used to determine the presence of RAR and RXR isoforms in the presence of other retinoid receptors or related intracellular receptors.

Thus, the present invention also provides isotopically labeled and radiolabeled compounds, and methods for their synthesis, including deuterium, tritium, carbon 13 and carbon 14 labeled homologs. In a preferred aspect, the labeled compounds of the present invention display a specific activity of at least 15 Ci/mmol, and more preferably at least 25 Ci/mmol, and most preferably, at least 40 Ci/mmol. Such labeled compounds will also prove useful in the identification of compound metabolites in animal metabolism studies.

Due to the selective specificity of the compounds of this invention for retinoid receptors, these compounds can also be used to purify samples of RARs and RXRs in vitro. Such purification can be carried out by mixing samples containing retinoid receptors with one of more of the compounds of the present invention, so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

The compounds of the present invention also include racemate, individual stereoisomers and mixtures thereof. These isomers are then isolated by standard resolution techniques, including fractional crystallization and chiral column chromatography.

The compounds and pharmaceutical compositions of the present invention can advantageously be used in the treatment of the diseases and conditions described herein. In this regard, the compounds and compositions will prove particularly useful in the treatment of skin-related diseases and conditions, such as acne, psoriasis, and photo damage, cancerous and precancerous conditions, diseases of the eye, cardiovascular diseases, inflammatory and neurodegenerative diseases, diseases associated with human papilloma virus, improper pituitary function, modulation of apoptosis, diseases of the immune system, wound healing and restoration of hair growth.

Furthermore, the compounds and pharmaceutical compositions of the present invention possess a number of advantages over previously identified retinoid compounds. For example, the compounds are extremely potent activators of RARs and RXRs as demonstrated in the co-transfection assay further described herein, preferably displaying 50% maximal activation (i.e., $EC_{50}$) of one or more of the retinoid receptors at a concentration of less than 100 nM, more preferably at a concentration of less than 50 nM, more preferably yet at a concentration of less than 20 nM, and most preferably at a concentration of less than 10 nM. Also, the RAR and RXR selective compounds of the present invention preferentially activate one subfamily of retinoid receptors at a potency level at least 2 times greater, preferably at least 5 times greater, more preferably at least 10 times greater, and most preferably at a potency level at least 100 times greater than the other subfamily of retinoid receptors. In addition, the compounds of the present invention also are easier to synthesize, provide greater stability and bioavailability, and appear to be less teratogenic in comparison to all-trans retinoic acid and 9-cis retinoic acid, known RAR and RXR active compounds, respectively.

The invention will be further illustrated by reference to the following non-limiting Examples.

EXAMPLES 1–2

(2E, 4E, 6E)-7-(3,5-Di-t-butylphenyl)-3-methylocta-2,4,6-trienoic acid (9) and (2E, 4E, 6Z)-7-(3,5-di-t-butylphenyl)-3-methylocta-2,4,6-trienoic acid (10), prepared according to Scheme 1 illustrated and described below.

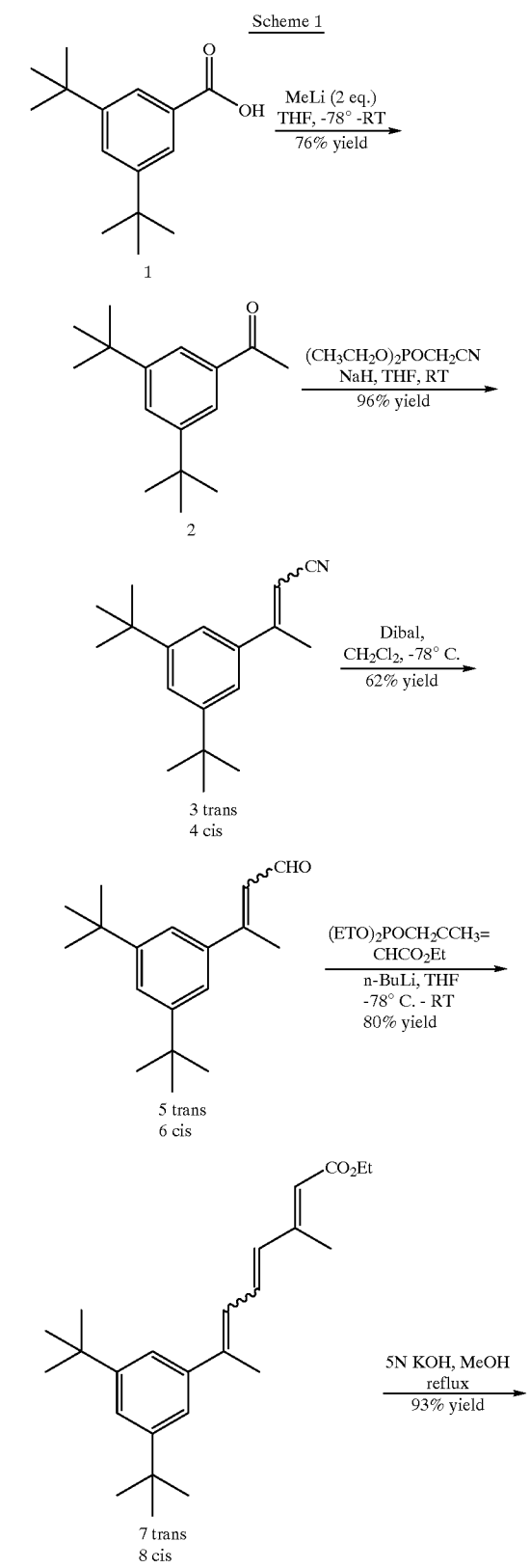

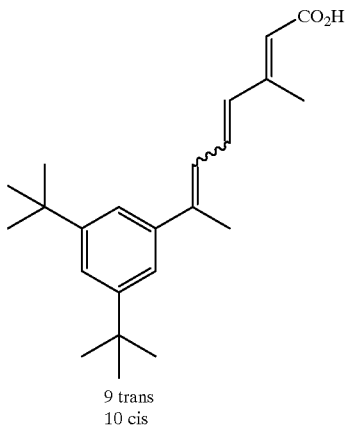

9 trans
10 cis 3,5-Di-t-butylacetophenone (2). To 20 g (85.5 mmol) of 3,5-di-tertbutylbenzoic acid 1 in 100 mL of dry THF at −78° C. was added 94.0 mL (188.0 mmol) of a 2 N ether solution of MeLi. The reaction mixture was slowly warmed to room temperature and stirred for an additional 30 min., then poured into saturated aqueous NH$_4$Cl (200 mL). The organic product was extracted with hexanes (2×100 mL) dried (MgSO$_4$), filtered, concentrated and purified by chromatography (SiO$_2$, 2 EtOAc-hexanes) to give 15 g (64.7 mmol) of ketone 2 (75.7% yield): TLC (5% EtOAc-95% hexanes) R$_f$ 0.8; $^1$H-NMR (CDCl$_3$)δ 1.39 (s, 18H, 6(CH$_3$)), 2.61 (s, 3H, CH$_3$), 7.64 (t, J=1 Hz, 1H, Ar—H), 7.80 (d, J=1 Hz, 2H, Ar—H).

3-(3,5-Di-t-butylphenyl)but-2-enitrile (3) (trans) and (4) (cis). To 2.43 g (13.7 mmol) of diethylcyanomethyl phosphonate in 10 mL of dry THF was added 440 mg (10.96 mmol) of NaH (60% in mineral oil). The reaction was stirred for 30 min. followed by addition of 1.59 g (6.85 mmol) of ketone 2 in 5 mL of dry THF. After stirring for 12 h, the mixture was quenched with saturated aqueous NH$_4$Cl (50 mL) and the products were extracted with ether (2×50 mL). The ether extracts were washed (water then brine), dried (MgSO$_4$), filtered, concentrated and purified by preparative TLC (SiO$_2$, 2.5% EtOAc-hexanes) to give 1.1 g (4.4 mmol) of the trans isomer 3 and 104 mg (0.4 mmol) of the cis isomer 4 (70% combined yield). Trans isomer 3: TLC (5% EtOAc-95% hexanes) R$_f$ 0.9; $^1$H-NMR (CDCl$_3$)δ 1.32 (s, 18H, 6(CH$_3$), 2.49 (s, 3H, CH$_3$), 5.59 (s, 1H, =CH), 7.25 (d, J=1 Hz, 2H, Ar—H), 7.50 (d, J=1 Hz, 1H, Ar—H). Cis isomer 4: TLC (5% EtOAc-95% hexanes) R$_f$ 0.8; $^1$H-NMR (CDCl$_3$)δ 1.42 (s, 18H, 6(CH$_3$), 2.31 (s, 3H, CH$_3$), 5.34 (s, 1H, =CH), 7.39 (d, J=1 Hz, 2H, Ar—H), 7.49 (d, J=1 Hz, 1H, Ar—H).

3-(3,5-Di-t-butylphenyl)but-2-enal (5) (trans isomer). To 736 mg (2.89 mmol) of 3 in 5 mL of CH$_2$Cl$_2$ at −78° C. was added 2.31 mL (3.47 mmol) of a 1.5 M solution of DIBAL in toluene. After stirring for 15 min. at −78° C., the reaction mixture was quenched with 10 mL of a saturated aqueous solution of Rochelle salt. The product was extracted with ether (2×20 mL), washed (water, then brine), dried (MgSO$_4$), filtered, concentrated and purified by chromatography (SiO$_2$, 3% EtOAc-hexanes) to give 462.3 mg (1.80 mmol) of 5 (62% yield): TLC (10% EtOAc-90% hexanes) R$_f$ 0.5; $^1$H-NMR (CDCl$_3$)δ 1.34 (s, 18H, 6(CH$_3$)), 2.59 (s, 3H, CH$_3$), 6.50 (d, J=8.0 Hz, 1H, =CH), 7.39 (d, J=1 Hz, 2H, Ar—H), 7.51 (d, J=1 Hz, 1H, Ar—H), 10.18 (d, J=8.0 Hz, 1H, CHO).

3-(3,5-Di-t-butylphenyl)but-2-enal (6) (cis isomer). The cis isomer 6 was prepared from the corresponding cis isomer 4 using the same method as described for 5: TLC (10% EtOAc-90% hexanes) R$_f$ 0.55; $^1$H-NMR (CDCl$_3$)δ 1.34 (s, 18H, 6(CH$_3$)), 2.34 (s, 3H, CH$_3$), 6.12 (d, J=8.0 Hz, 1H, =CH), 7.10 (d, J=1 Hz, 2H, Ar—H), 7.46 (t, J=1 Hz, 1H, Ar—H), 9.45 (d, J=8.0 Hz, 1H, CHO).

Ethyl (2E, 4E, 6E)-7-(315-di-t-butylphenyl)-3-methylocta-2,4,6-trienoate (7). To 790 mg (3.0 mmol) of triethyl-3-methyl-4-phosphonocrotonate in 8 mL of dry THF at −78° C. was added 1.2 mL of a 2.5 M nBuLi solution in hexanes. After stirring for 15 min., the solution containing the ylide of triethylphosphonocrotonate was added to 258 mg (1.0 mmol) of the trans isomer 5 in 8 mL of dry THF at −78° C. The reaction mixture was warmed to RT, quenched with saturated aqueous NH$_4$Cl (20 mL) and the products were extracted with ether (2×50 mL). The ether extracts were washed (water, then brine), dried (MgSO$_4$), filtered, concentrated and purified by column chromatography (SiO$_2$, 5% EtOAc-hexanes) to give 294 mg (0.8 mmol) of the E,E,Eisomer of 7 (49% yield): TLC (5% EtOAc-95% hexanes) R$_f$ 0.78; $^1$H-NMR (CDCl$_3$)δ 1.30 (t, J=7.7 Hz, 3H, CH$_2$CH$_3$), 1.34 (s, 18H, 6(CH$_3$)), 2.28, (s, 3H, CH$_3$), 2.39 (s, 3H, CH$_3$), 4.17 (m, 2H, CH$_2$CH$_3$), 5.82 (s, 1H, =CH), 6.40 (d, J=15 Hz, 1H, =CH), 6.54 (d, J=15 Hz, 1H, =CH), 7.04 (m, 1H, =CH), 7.21 (d, J=1 Hz, 2H, Ar—H), 7.39 (d, J=1 Hz, 1H, Ar—H).

Ethyl (2E, 4E, 6Z)-7-(3,5-di-t-butylphenyl)-3-methylocta-2,4,6-trienoate (8). The 2E, 4E, 6Z isomer 8 was prepared in the same manner as the 2E,4E,6E-isomer 7, except that 6 was used instead of the 5: TLC (5% EtOAc-95% hexanes) R$_f$ 0.82; $^1$H-NMR (CDCl$_3$)δ 1.27 (t, J=7.7 Hz, 3H, CH$_2$CH$_3$), 1.34 (s, 18H, 6(CH$_3$)), 2.17, (s, 3H, CH$_3$), 2.22 (s, 3H, CH$_3$), 4.15 (m, 2H, CH$_2$CH$_3$), 5.74 (s, 1H, =CH), 6.26 (dd, J=8 Hz, 2H, =CH), 6.80 (m, 1H, =CH), 7.10 (d, J=1 Hz, 2H, Ar—H), 7.37 (t, J=1 Hz, 1H, Ar—H).

(2E, 4E, 6E)-7-(3,5-Di-t-butylphenyl)-3-methylocta-2,4,6-trienoic acid (9). To 180 mg (0.49 mmol) of the 2E, 4E, 6E-ethyl ester 7 in 5 mL of MeOH was added 1 mL of 5N aqueous NaOH solution. The mixture was heated to reflux for 10 min., cooled to RT, acidified with 20% aqueous HCl solution and the organics extracted with ether (2×10 mL). The ether layer was washed (H$_2$O, brine), dried (MgSO$_4$), filtered and concentrated. Purification by column chromatography (SiO$_2$, 20% EtOAc-hexanes) gave 157 mg (0.46 mmol) of the 2E,4E,6E-isomer 9 (93% yield): TLC (10% MeOH-90% CHCl$_3$) R$_f$ 0.6; mp 196–198° C.; $^1$H-NMR (CDCl$_3$) δ 1.35 (s, 18H, 6(CH$_3$)), 2.29, (s, 3H, CH$_3$), 2.41 (s, 3H, CH$_3$), 5.84 (s, 1H, =CH), 6.41 (d, J=15 Hz, 1H, =CH), 6.54 (d, J=15 Hz, 1H, =CH), 7.08 (m, 1H, =CH), 7.32 (d, J=1 Hz, 2H, Ar—H), 7.39 (t, J=1 Hz, 1H, Ar—H).

(2E, 4E, 6Z)-7-(3,5-Di-t-butylphenyl)-3-methylocta-2,4,6-trienoic acid (10). The 2E, 4E, 6Z-isomer 10 was prepared in the same manner as 9 except that 8 was used instead of 7: TLC (10% MeOH-90% CHCl$_3$) R$_f$ 0.57; mp 221–222° C.; $^1$H-NMR (CDCl$_3$)δ 1.34 (s, 18H, 6(CH$_3$)), 2.18, (s, 3H, CH$_3$), 2.23 (s, 3H, CH$_3$), 5.77 (s, 1H, =CH), 6.27 (m, 2H, =CH), 6.84 (m, 1H, =CH), 7.10 (d, J=1 Hz, 2H, Ar—H), 7.37 (t, J=1 Hz, 1H, Ar—H).

EXAMPLE 3

(2E, 4E)-7-(3,5-Di-t-butylphenyl)-3-methylocta-2,4-dienoic acid (14), prepared according to Scheme 2 illustrated and described below.

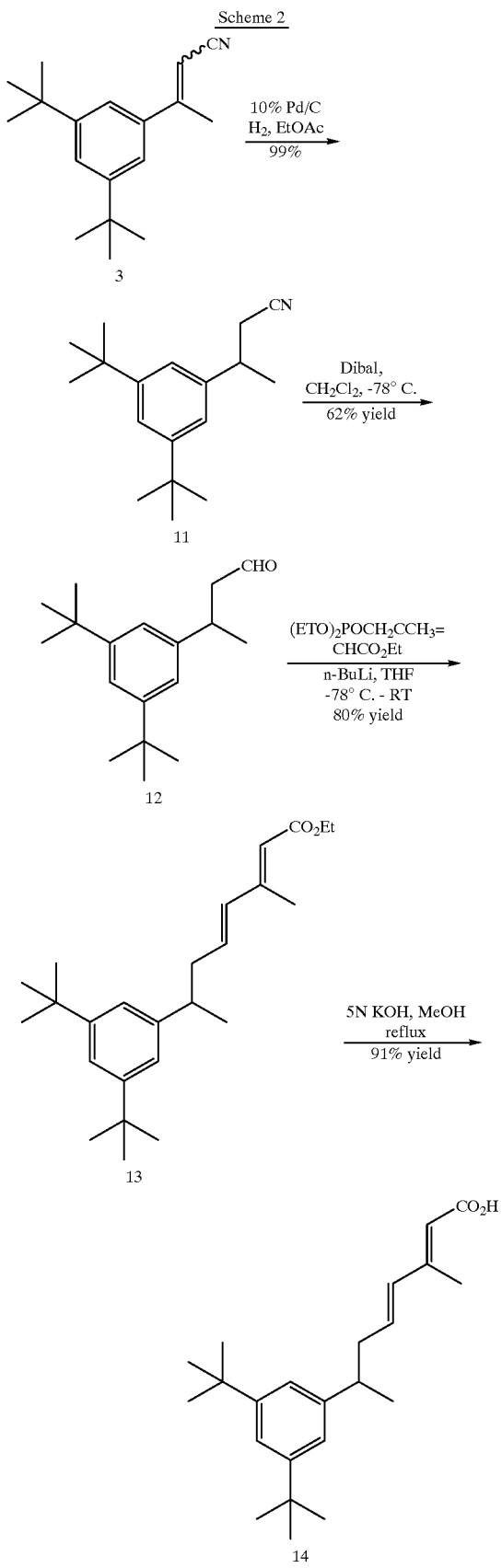

3-(3,5-Di-t-butylphenyl)butanitrile (11). To 300 mg (1.18 mmol) of 3-(3,5-di-t-butylphenyl)-but-2-enitrile 3 in 5 mL of EtOAc was added 20 mg (catalytic quantity) of 10% Pd/C. The mixture was placed under vacuum for 0.5 min., followed by addition of $H_2$ gas. After stirring for 2 h under $H_2$ gas, the solution was filtered through celite, the celite washed with EtOAc (3×5 mL) and the solution concentrated to give 300 mg (1.17 mmol) of the reduced product 11 (99% yield): TLC (5% EtOAc-95% hexanes) $R_f$ 0.8; $^1$H-NMR (CDCl$_3$)δ 1.34 (s, 18H, 6(CH$_3$)), 1.50 (d, 3H, CH$_3$), 2.60 (m, 2H, CH$_2$), 3.15 (m, 1H, CH), 7.05 (d, J=1 Hz, 2H, Ar—H), 7.33 (t, J=1 Hz, 1H, Ar—H).

3-(3,5-Di-t-butylphenyl)butanal (12). To 300 mg (1.17 mmol) of the nitrile 11 in 5 mL of CH$_2$Cl$_2$ at −78° C. was added 0.93 mL (1.4 mmol) of a 1.5 M DIBAL solution in toluene. The reaction mixture was stirred for 5 min., quenched with saturated aqueous NH$_4$Cl (10 mL), extracted with ether (2×20 mL), dried (MgSO$_4$), filtered, concentrated and purified by chromatography (SiO$_2$, 5% EtOAc-hexanes) to give 188 mg (0.72 mmol) of the desired aldehyde 12 (62% yield): TLC (5% EtOAc-95% hexanes) $R_f$ 0.8; $^1$H-NMR (CDCl$_3$)δ 1.34 (s, 18H, 6(CH$_3$)), 1.35 (d, 3H, CH$_3$), 2.70 (m, 2H, CH$_2$), 3.36 (m, 1H, CH), 7.06 (d, J=1 Hz, 2H, Ar—H), 7.28 (t, J=1 Hz, 1H, Ar—H), 9.70 (t, 1H, CHO).

Ethyl (2E, 4E)-7-(3.5-di-t-butylphenyl)-3-methylocta-2,4-dienoate (13). Compound 13 was prepared from 12 in a similar manner as described for compound 7: TLC (5% EtOAc-95% hexanes) $R_f$ 0.88; $^1$H-NMR (CDCl$_3$)δ 1.30 (m, 6H, CH$_2$CH$_3$+CH$_3$), 1.34 (s, 18H, 6(CH$_3$)), 2.20, (s, 3H, CH$_3$), 2.40 (m, 2H, CH$_2$), 2.85 (m, 1H, CH), 4.14 (m, 2H, CH$_2$CH$_3$), 5.62 (s, 1H, =CH), 6.03 (m, 2H, =CH), 7.00 (d, J=1 Hz, 2H, Ar—H), 7.24 (t, J=1 Hz, 1H, Ar—H).

(2E, 4E)-7-(3,5-Di-t-butylphenyl)-3-methylocta-2,4-dienoic acid (14). Compound 14 was prepared from 13 in a similar manner as described for compound 9: TLC (10% MeOH-90% CHCl$_3$) $R_f$ 0.5; mp 127–128° C.; $^1$H-NMR (CDCl$_3$)δ 1.28 (d, J=8 Hz, 3H, CH$_3$), 1.32 (s, 18H, 6(CH$_3$)), 2.23, (s, 3H, CH$_3$), 2.46 (m, 2H, CH$_2$), 2.86 (m, 1H, CH), 5.69 (s, 1H, =CH), 6.10 (m, 2H, =CH), 7.01 (d, J=1 Hz, 2H, Ar—H), 7.26 (t, J=1 Hz, 1H, Ar—H).

EXAMPLE 4

(2E, 4E, 6Z)-7-(3,5-Di-t-butylphenyl)-3-methylocta-2,4,6-trienoic acid (10), alternative preparation of Compound (10) according to Scheme 3 illustrated and described below.

Scheme 3

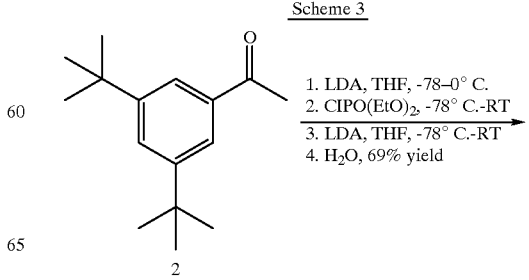

-continued

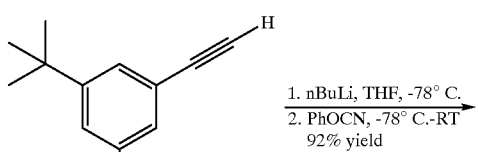

1. nBuLi, THF, -78° C.
2. PhOCN, -78° C.-RT
92% yield

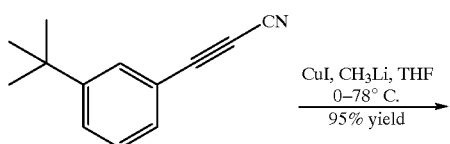

CuI, CH₃Li, THF
0-78° C.
95% yield

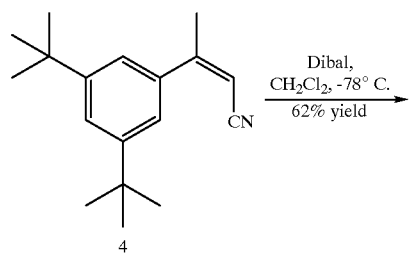

Dibal,
CH₂Cl₂, -78° C.
62% yield

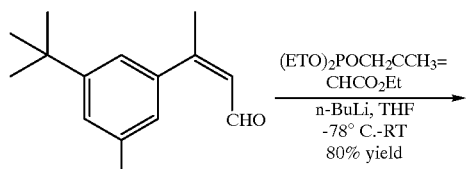

(ETO)₂POCH₂CCH₃=
CHCO₂Et
n-BuLi, THF
-78° C.-RT
80% yield

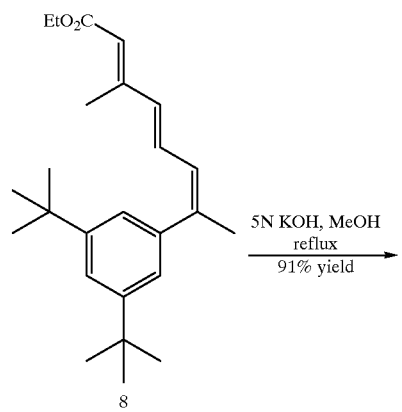

5N KOH, MeOH
reflux
91% yield

-continued

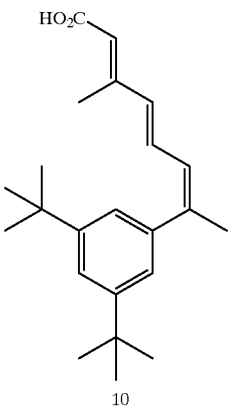

1,3-Di-t-butyl-5-ethynylbenzene (15). To 9.86 mL (24.7 mmol) of a 2.5 N LDA solution in THF at -78° C. was added 4.75 g (20.47 mmol) of ketone 2 (from EXAMPLES 1–2) in 3 mL of dry THF. After stirring for 30 min., 2.96 mL (20.47 mmol) of diethylphosphonyl-chloride was added and the reaction mixture was warmed to RT for 1 h. The reaction mixture was again cooled to -78° C. followed by addition of 19.7 mL (49.2 mmol) of a 2.5 N LDA solution in THF and warmed to RT. Water (50 mL) was added and the mixture was extracted with hexanes (2×40 mL). The combined organic extract was washed (water, then brine), dried (MgSO₄), filtered, concentrated and purified by column chromatography (SiO₂, 2% EtOAc-hexanes) to give 3.02 g (14.1 mmol) of compound 15 (69% yield): TLC (hexanes) $R_f$ 0.9; ¹H-NMR (CDCl₃)δ 1.31 (s, 18H, 6(CH₃)), 3.02 (s, 1H, C≡CH), 7.35 (d, J=1 Hz, 2H, Ar—H), 7.42 (t, J=1 Hz, 1H, Ar—H).

3-(3,5-Di-t-butylphenyl)propynitrile (16). To 1.67 g (7.80 mmol) of propyne 15 in 25 mL of dry THF at -78° C. was added 3.75 mL (9.38 mmol) of nBuLi (2.5 M in hexanes). After stirring for 15 min., 1.12 g (9.41 mmol) of PhOCN was added and the reaction mixture was warmed to RT. The mixture was quenched by addition of 25 mL of aqueous 6N NaOH, extracted (EtOAc, 2×25 mL), washed (water, then brine), dried (MgSO₄), filtered, concentrated and purified by column chromatography (SiO₂, 5% EtOAc-hexane) to give 1.71 g (7.16 mmol) of 16 as a white solid (92% yield): TLC (hexanes) $R_f$ 0.4; ¹H-NMR (CDCl₃)δ 1.32 (s, 18H, 6(CH₃)), 7.45 (d, J=1 Hz, 2H, Ar—H), 7.58 (t, J=1 Hz, 1H, Ar—H).

3-(3,5-Di-t-butylphenyl)but-2-enitrile (4) (cis isomer). A 250 mL flame dried round bottom flask was charged with 3.27 g (17.17 mmol) of anhydrous copper iodide and 25 mL of dry THF. The mixture was cooled to 0° C., followed by slow addition of 24.5 mL (34.3 mmol) of MeLi (1.4 M in ether). After the solution became clear and colorless, it was cooled to -78° C. and a solution of 1.71 g (7.16 mmol) of 16 in 10 mL of dry THF was added dropwise. The mixture was stirred at -78° C. for 45 min. and quenched with 40 mL of a 1:1 mixture of MeOH and saturated aqueous NH₄Cl solution. The product was extracted with EtOAc (2×40 mL), washed (2% NaOH followed by sat. NH₄Cl, then water, then brine), dried (MgSO₄), filtered, concentrated and purified through a short silica gel pad to give 1.64 g (6.80 mmol) of the cis isomer 4 (95% yield): TLC (5% EtOAc-95% hexanes) $R_f$ 0.8; ¹H-NMR (CDCl₃)δ 1.42 (s, 18H, 6(CH₃)), 2.31 (s, 3H, CH₃), 5.34 (s, 1H, =CH), 7.39 (d, J=1 Hz, 2H, Ar—H), 7.49 (d, J=1 Hz, 1H, Ar—H).

The remaining synthesis of Compounds 6, 8 and final product 10 were performed as described in EXAMPLES 1–2 above.

EXAMPLES 5–6

(2E, 4E, 6E)-7-(3,5-Di-t-butylphenyl)-3-methyldeca-2,4,6-trienoic acid (27) and (2E, 4E, 6Z)-7-(3,5-di-t-butylphenyl)-3-methyldeca-2,4,6-trienoic acid (28), prepared according to Scheme 4 illustrated and described below.

Scheme 4

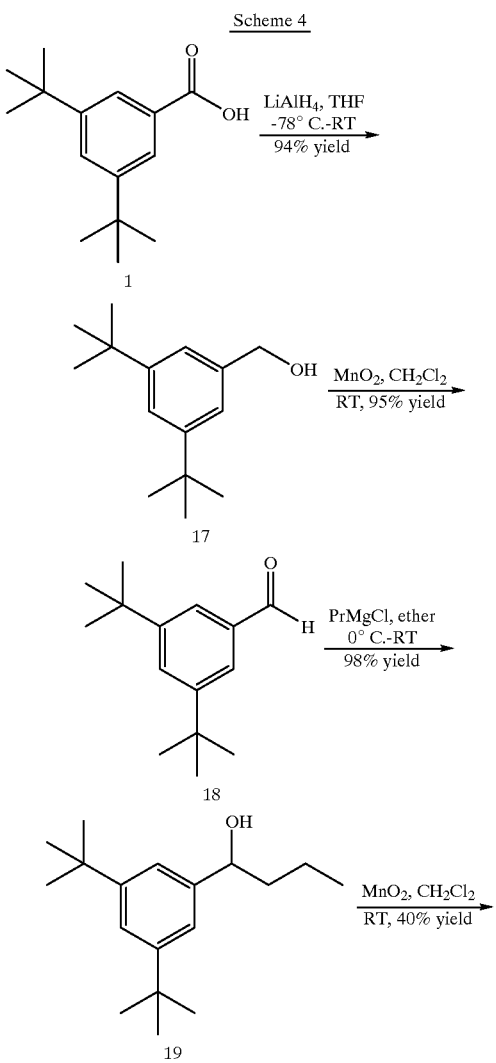

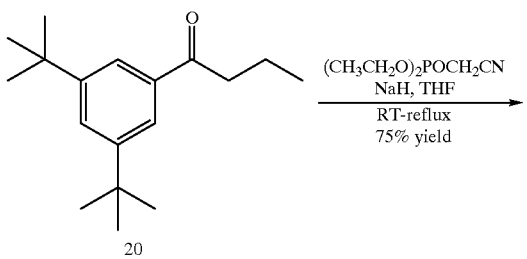

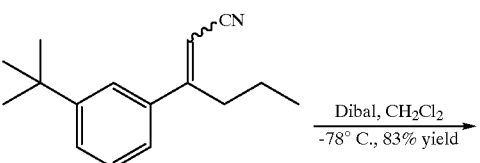

21 trans
22 cis

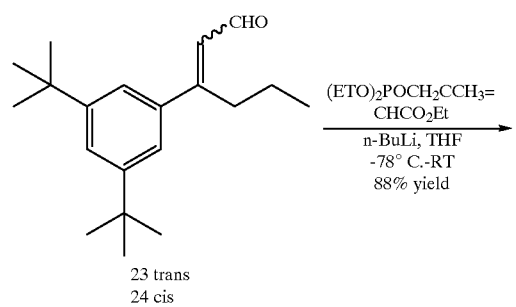

23 trans
24 cis

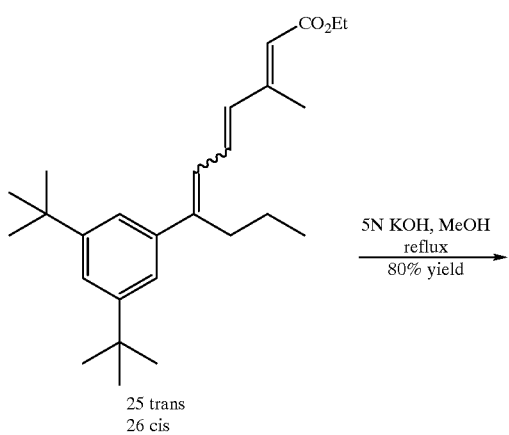

25 trans
26 cis

-continued

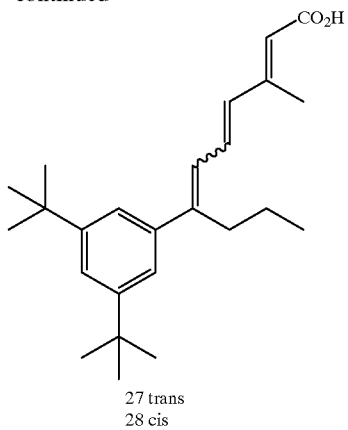

27 trans
28 cis 3,5-Di-t-butylbenzyl alcohol (17). To 10.0 g (42.7 mmol) of acid 1 in 20 niL of dry THF at 0° C. was added 42.7 mL (42.7 mmol) of LAH (1.0 M in THF). The reaction mixture was warmed to 50° C. and stirred for 15 min. After cooling the reaction to RT, 20% aqueous HCl was added until the solution turned clear. The solution was extracted with EtOAc (2×50 mL), and the combined EtOAc extract was washed (water, then brine), dried (MgSO$_4$), filtered and concentrated to give 8.8 g (40.0 mmol) of 17 (94% yield): The product was directly used in the next step. TLC (20% EtOAc-80% hexanes) R$_f$ 0.4; $^1$H-NMR (CDCl$_3$)δ 1.33 (s, 18H, 6(CH$_3$)), 4.68 (s, 2H, CH$_2$) 7.22 (d, J=1 Hz, 2H, Ar—H), 7.38 (t, J=1 Hz, 1H, Ar—H). 3,5-Di-t-butylbenzaldehyde (18). To 8.8 g (40.0 mmol) of alcohol 17 in 20 mL of CH$_2$Cl2 was added 50.0 g (575 mmol) of MnO2. The reaction mixture was vigorously stirred for 8 h and filtered through a pad consisting of a top layer of celite and a bottom layer of silica. The filter was washed repeatedly with 50 mL aliquots of CH$_2$Cl$_2$ until no more product eluted from the filter. The resulting compound 18 (8.3 g (38.1 mmol)) was determined to be pure by IHNMR and was used directly in the next step (95% yield): TLC (20% EtOAc-80% hexanes) R$_f$ 0.6; $^1$H-NMR (CDCl$_3$)δ 1.34 (s, 18H, 6(CH$_3$)), 7.72 (m, 3H, Ar—H), 10.01 (s, 1H, CHO). 1-(3,5-Di-t-butylphenyl)butan-1-ol (19). To 2.0 g (9.17 mmol) of aldehyde 18 in 10 mL of dry ether at 0° C. was added 5.5 mL (11.0 mmol) of propylmagnesium chloride (2.0 M in ether). The reaction mixture was warmed to RT and quenched with water (50 mL), extracted (ether, 2×50 S mL), washed (water then brine), dried (MgSO$_4$), filtered and concentrated to give 2.37 g (9.05 mmol) of alcohol 19 (pure by $^1$H-NMR) which was directly used in the next step (98% yield): TLC (20% EtOAc-80% hexanes) R$_f$ 0.5; $^1$H-NMR (CDCl$_3$)δ 0.96 (t, 3H, CH$_2$CH$_3$), 1.34 (s, 18H, 6(CH$_3$)), 1.66 (m, 2H, CH$_2$), 1.84 (m, 1H, CH), 4.66 (m, 1H, CHOH), 7.18 (d, J=1 Hz, 2H, Ar—H), 7.34 (t, J=1 Hz, 1H, Ar—H).
1-(3,5-Di-t-butylphenyl)butan-1-one (20). To 2.37 g (9.05 mmol) of alcohol 19 in 18 mL of CH$_2$Cl$_2$ was added 7.86 g (90.45 mmol) of MnO$_2$. The reaction mixture was stirred for 3 h, then filtered (celite over silica gel pad) and the pad was washed repeatedly with 20 mL aliquots of CH$_2$Cl$_2$. After concentration, ketone 20 was purified by chromatography (SiO$_2$, 3% EtOAc-hexanes) to give 941 mg (3.62 mmol) of 20 (40% yield): TLC (10% EtOAc-90% hexanes) Rf 0.7; $^1$H-NMR (CDCl$_3$)δ 1.01 (t, 3H, CH$_2$CH$_3$), 1.34 (s, 18H, 6(CH$_3$)), 1.78 (m, 2H, CH$_2$CH$_3$), 2.96 (t, J=7 Hz, 2H, CH$_2$CH$_2$CH$_3$), 7.63 (t, J=1 Hz, 1H, Ar—H), 7.83 (d, J=1 Hz, 2H, Ar—H).

3-(3,5-Di-t-butylphenyl)hex-2-enitrile (21) (trans) and (22) (cis). To 661 mg (3.73 mmol) of diethylcyanomethylphosphonate in 5 mL of dry THF was added 127 mg (3.17 mmol) of sodium hydride (60% dispersion in mineral oil). The mixture was stirred for 5 min., followed by addition of 484 mg (1.87 mmol) of ketone 20 in 2 mL of dry THF. The reaction was heated to reflux for 30 m, cooled to RT, quenched with saturated aqueous NH$_4$Cl (15 mL), extracted with ether (2×15 mL), washed (water then brine), dried (MgSO$_4$), filtered and concentrated. Purification by chromatography (preparative TLC, SiO$_2$, 10% EtOAc-hexanes) gave 329 mg (1.16 mmol) of the trans isomer 21 and 70.5 mg (0.25 mmol) of the cis isomer 22 (75% combined yield). Trans isomer 21 TLC (10% EtOAc-90% hexanes) R$_f$ 0.8; $^1$H-NMR (CDCl$_3$)δ 0.97 (t, J=7 Hz, 3H, CH$_2$CH$_3$), 1.33 (s, 18H 6(CH$_3$)), 1.54 (m, 2H, CH$_2$CH$_2$CH$_3$), 2.88 (t, J=7 Hz, 2H, CH$_2$CH$_2$CH$_3$), 5.50 (s, 1H, =CH), 7.23 (d, J=1 Hz, 2H, Ar—H), 7.50 (t, J=1 Hz, 1H, Ar—H). Cis isomer 22: TLC (10% EtOAc-90% hexanes) R$_f$ 0.9; $^1$H-NMR (CDCl$_3$)δ 0.93 (t, J=7 Hz, 3H, CH$_2$CH$_3$), 1.34 (s, 18H 6(CH$_3$)), 1.48 (m, 2H, CH$_2$CH$_2$CH$_3$), 2.57 (t, J=7 Hz, 2H, CH$_2$CH$_2$CH$_3$), 5.32 (s, 1H, =CH), 7.28 (d, J=2 Hz, 2H, Ar—H), 7.45 (t, J=2 Hz, 1H, Ar—H).
3-(3,5-Di-t-butylphenyl)hex-2-enal (23) (trans). To 166 mg (0.59 mmol) of nitrile 21 in 4 mL of CH$_2$Cl$_2$ at −78° C. was added 0.59 mL (0.88 mmol) of DIBAL (1.5 M in toluene). The reaction mixture was stiffed for 10 m and quenched with 10 mL of a saturated aqueous solution of Rochelle salt. The product was extracted with ether (2×20 mL), washed (water then brine), dried (MgSO$_4$), filtered, concentrated and purified by chromatography (preparative TLC, SiO$_2$, 3% EtOAc-hexanes) to give 141 mg (0.49 mmol) of 23 as an oil (83% yield)-TLC (10% EtOAc- 90% hexanes) R$_f$ 0.7; $^1$H-NMR (CDCl$_3$)δ 0.97 (t, J=7 Hz, 3H, CH$_2$CH$_3$), 1.34 (s, 18H, 6(CH$_3$)), 1.57 (m, 2H, CH$_2$CH$_2$CH$_3$), 3.03 (t, J=7 Hz, 2H, CH$_2$CH$_2$CH$_3$), 6.32 (d, J=8 Hz, 1H, =CH), 7.33 (d, J=1 Hz, 2H, Ar—H), 7.48 (t, J=1 Hz, 1H, Ar—H), 10.15 (d, J=8 Hz, 1H, CHO). 3-(3,5-Di-t-butylphenyl)hex-2-enal (24) (cis). Compound 24 was prepared in the same manner as 23 except that the cis isomer 22 was used instead of 21: TLC (10% EtOAc-90% hexanes) R$_f$ 0.8; $^1$H-NMR (CDCl$_3$)δ 0.94 (t, J=7 Hz, 3H, CH$_2$CH$_3$), 1.34 (s, 9H, CH$_3$), 1.35 (s, 9H, CH$_3$), 1.51 (m, 2H, CH$_2$CH$_2$CH$_3$), 2.58 (t, J=7 Hz, 2H, CH$_2$CH$_2$CH$_3$), 6.10 (d, J=8 Hz, 1H, =CH), 7.04 (d, J=2 Hz, 2H, Ar—H), 7.43 (t, J=2 Hz, 1H, Ar—H), 9.42 (d, J=8 Hz, 1H, CHO).
Ethyl (2E, 4E, 6E)-7-(3,5-di-t-butylphenyl)-3-methyldeca-2,4,6-trienoate (25). To 391 mg (1.48 mmol) of triethyl-3-methyl-4-phosphonocrotonate in 5 mL of dry THF at −78° C. was added 0.59 mL (1.48 mmol) of a 2.5 M nBuLi solution in hexanes and 2.5 mL of DMPU. After stirring for 15 min., the solution containing the ylide of triethylphosphonocrotonate was added to 141 mg (0.49 mmol) 23 in 5 mL of dry THF at −78° C. The reaction mixture was warmed to RT, quenched with saturated aqueous NH$_4$Cl (20 mL) and the products were extracted with ether (2×25 mL). The ether extracts were washed (water, then brine), dried (MgSO$_4$), filtered, concentrated and purified by column chromatography (SiO$_2$, 5% EtOAc-hexanes) to give 171 mg (0.43 mmol) of the all-trans isomer 25 (88% yield): TLC (5% EtOAc-95% hexanes) R$_f$ 0.5; $^1$H-NMR (CDCl$_3$)δ 0.94 (t, J=7 Hz, 3H, CH$_2$CH$_3$), 1.29 (t, J=7 Hz, 3H, CH$_2$CH$_3$), 1.34 (s, 18H, 6(CH$_3$)), 1.52 (m, 2H, CH$_2$CH$_2$CH$_3$), 2.39 (s, 3H, CH$_3$), 2.70 (t, J=7 Hz, 2H, CH$_2$CH$_2$CH$_3$), 4.18 (m, 2H, CH$_2$CH$_3$), 5.80 (s, 1H, =CH), 6.42 (d, J=15 Hz, 2H, =CH), 6.47 (d, J=15 Hz, 1H, =CH), 7.03 (m, 1H, =CH), 7.27 (d, J=1 Hz, 2H, Ar—H), 7.36 (t, J=1 Hz, 1H, Ar—H).

Ethyl (2E, 4E, 6E)-7-(3,5-di-t-butylphenyl)-3-methyldeca-2,4,6-trienoate (26). Compound 26 was prepared in the same manner as 25, except that the cis isomer 24 was used instead of 23: TLC (5% EtOAc-95% hexanes) R$_f$ 0.5; $^1$H-NMR (CDCl$_3$)δ 0.94 (t, J=7 Hz, 3H, CH$_2$CH$_3$), 1.29 (t, J=7 Hz, 3H, CH$_2$CH$_3$), 1.33 (s, 18H$^6$(CH$_3$)), 1.44 (m, 2H, CH$_2$CH$_2$CH$_3$), 2.15 (s, 3H, CH$_3$), 2.48 (t, J=7 Hz, 2H, CH$_2$CH$_2$CH$_3$), 4.16 (m, 2H, —COCH$_2$CH$_3$), 5.73 (s, 1H, =CH), 6.22 (d, J=11 Hz, 1H, =CH), 6.26 (d, J=11 Hz, 1H, =CH), 6.74 (dd, J=11 Hz, 1H, =CH), 7.26 (d, J=2 Hz, 2H, Ar—H), 7.34 (t, J=2 Hz, 1H, Ar—H).

(2E, 4E, 6E)-7-(3,5-Di-t-butylphenyl)-3-methyldeca-2,4,6-trienoic acid (27). To 171 mg (0.44 mmol) of 25 in 5 mL of MeOH was added 1 mL of 5N aqueous NaOH solution. The mixture was heated to reflux for 10 min., cooled to RT, acidified with 20% aqueous HCl solution, and the organics extracted with ether (2×10 mL). The ether layer was washed (water, then brine), dried (MgSO$_4$), filtered and concentrated. Purification by chromatography (preparative TLC, SiO$_2$, 20% EtOAc-hexanes) gave 28 mg (0.08 mmol) of the all-trans isomer of 27 (80% yield): TLC (10% MeOH-90% CHCl$_3$) R$_f$ 0.8; mp 143–144° C.; $^1$H-NMR (CDCl$_3$)δ 0.94 (t, J=7 Hz, 3H, CH$_2$CH$_3$), 1.34 (s, 18H, 6(CH$_3$)), 1.52 (m, 2H, CH$_2$CH$_2$CH$_3$), 2.40 (s, 3H, CH$_3$), 2.71 (t, J=7 Hz, 2H, CH$_2$CH$_2$CH$_3$), 5.84 (s, 1H, =CH), 6.41 (d, J=15 Hz, 1H, =CH), 6.47 (d, J=15 Hz; 1H, =CH), 7.08 (m, 1H, =CH), 7.26 (d, J=1 Hz, 2H, Ar—H), 7.37 (t, J=1 Hz, 1H, Ar—H).

(2E. 4E 6Z)-7-(3,5-Di-t-butylphenyl)-3-methyldeca-2,4,6-trienoic acid (28). Compound 28 was prepared in the same manner as 27 except that the cis isomer 26 was used instead of 25: TLC (10% MeOH-90% CHCl$_3$) R$_f$ 0.8; mp 166–169° C.; $^1$H-NMR (CDCl$_3$)δ 0.89 (t, J=7 Hz, 3H, CH$_2$CH$_3$), 1.31 (s, 9H, CH$_3$), 1.32 (s, 9H, CH$_3$), 1.42 (m, 2H, CH$_2$CH$_2$CH$_3$), 2.15 (s, 3H, CH$_3$), 2.49 (t, J=7 Hz, 2H, CH$_2$CH$_2$CH$_3$), 5.76 (s, 1H, =CH), 6.23 (d, J=11 Hz, 1H, =CH), 6.28 (d, J=15 Hz, 1H, =CH), 6.78 (dd, J=15 Hz, 1H, =CH), 7.04 (s, 2H, Ar—H), 7.35 (s, 1H, Ar—H).

EXAMPLES 7–8

(2E,4E,6E)-6-(6,8,-Di-t-butylchroman-4ylidene)-3-methylhexa-2,4,6-trienoic acid (39) and (2E,4E,6Z)-6-(6,8,-di-t-butylchroman-4-ylidene)-3-methylhexa-2,4,6-trienoic acid (40), prepared as illustrated and described in Scheme 5 below.

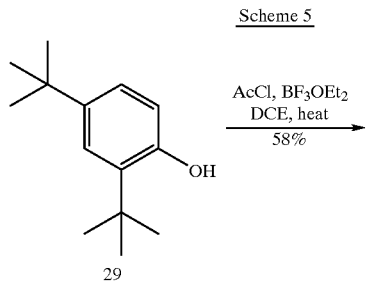

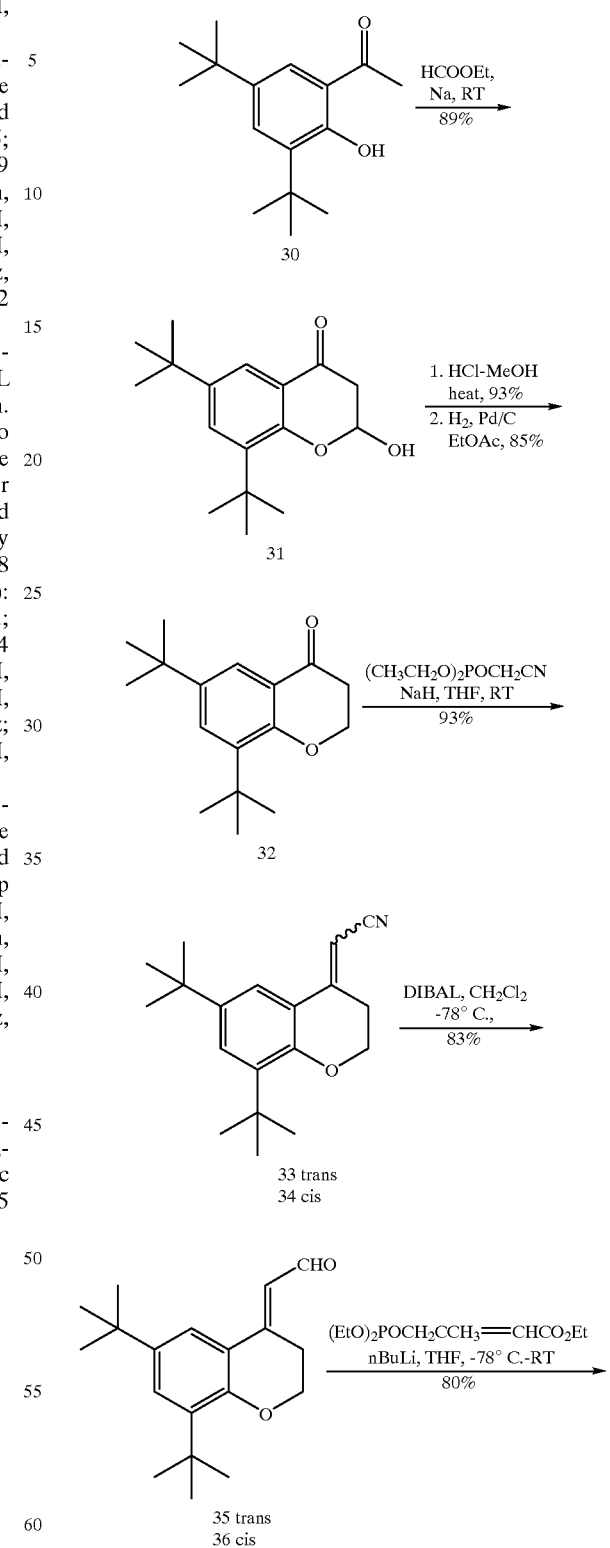

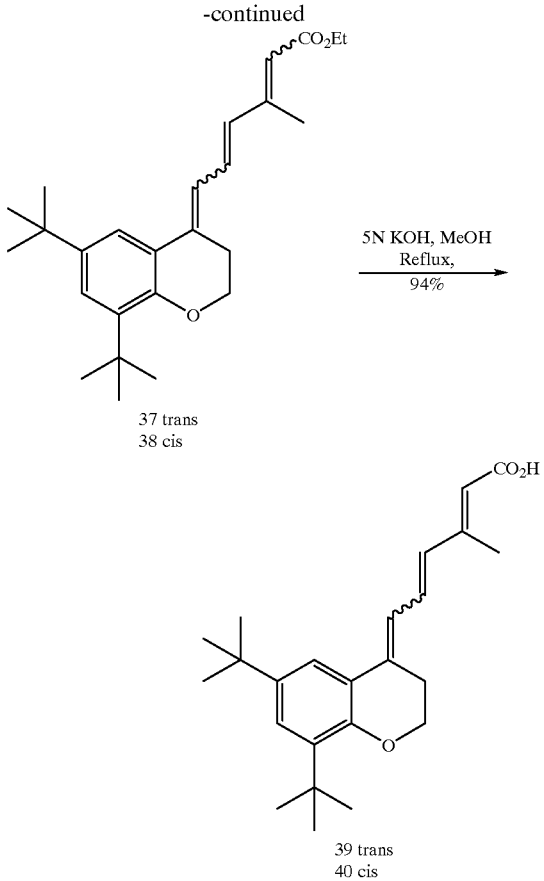

37 trans
38 cis 39 trans
40 cis 3,5-Di-t-butyl-2-hydroxyacetophenone (30). To 10 g (48.5 mmol) of 2,5-di-t-butylphenol 29 and 4.56 g (58.16 mmol) of acetyl chloride in 60 mL of dichloroethane was added 11.9 mL (97.0 mmol) of $BF_3 \cdot OEt_2$, and the mixture was heated to reflux for 10 min. The reaction was cooled and poured into 1:1 ice –20% aqueous HCl, stirred and extracted (2×100 mL of EtOAc). The organic extract was washed (water, then brine), dried ($MgSO_4$), concentrated and purified ($SiO_2$ chromatography, 5% EtOAc-hexanes) to give 7.0 g (28.22 mmol) of 30 as an oil (58% yield): TLC (5% % EtOAc-hexane) $R_f$ 0.1; $^1$H-NMR ($CDCl_3$)δ 1.32 (s, 9H, $CH_3$), 1.42 (s, 9H$^3$($CH_3$)), 2.68 (s, 3H, $CH_3$), 7.55 (m, 2H, Ar—H).

6,8-Di-t-butyl-2-hydroxychroman-4-one (31). To 1.8 g (78.26 mmol) of sodium metal in a flame dried 500 mL round bottom flask, was dropwise added 7.5 g (30.24 mmol) of phenol 30 in 120 mL of ethyl formate. Once addition was complete, the mixture was stirred at 40° C. for 1 h, then cooled to RT and poured into 1 N aqueous HCl. When the mixture became transparent, the organics were extracted (2×150 mL EtOAc), washed (water, then brine), dried ($MgSO_4$) and concentrated to give 7.4 g (26.81 mmol) of 31 as an oil (approximate yield, 89%). This product was used directly in the next step: TLC (20% EtOAc-hex) $R_f$ 0.4; $^1$H-NMR ($CDCl_3$)δ 1.30 (s, 9H 3($CH_3$)), 1.42 (s, 9H, $3CH_3$), 2.87 (dd, J=16.0, 5.5 Hz, 1H, $CH_2$), 3.01 (dd, J=16.0, 3.1 Hz, 1H, $CH_2$), 5.87 (dd, J=5.5, 3.3 Hz, 1H, CHOH), 7.58 (d, J=2.5 Hz, 1H, Ar—H), 7.79 (d, J=2.5 Hz, 1H, Ar—H).

4H-6,8-di-t-butyl-benzopyran-4-one (not shown). To 7.4 g (26.81 mmol) of 30 in 20 mL of MeOH was added 8 mL of aqueous 20% HCL and the mixture was heated at reflux for 20 min. After cooling to RT, water was added (30 mL) and the products were extracted (2×30 mL of EtOAc), washed (water, then brine), dried ($MgSO_4$), and concentrated to give ca 6.0 g (25.00 mmol) of 4H-6,8-di-t-butyl-benzopyran-4-one as an oil which after standing for several hours, solidified (approximate yield, 93%). This product was directly used in the next step: TLC (5% EtOAc-hex) $R_f$ 0.5; $^1$H-NMR ($CDCl_3$)δ 1.37 (s, 9H, $3CH_3$), 1.49 (s, 9H, $3CH_3$), 6.35 (d, J=5.6 Hz, 1H, CH=CH), 7.70 (d, J=2.4 Hz, 1H, Ar—H), 7.91 (d, J=5.6 Hz, 1H, CH=CH), 8.10 (d, J=2.4 Hz, 1H, Ar—H).

6,8-Di-t-butyl-chroman-4-one (32). To 1.0 g (3.87 mmol) of 4H-6,8-di-t-butyl-benzopyran-4-one in 8 mL of EtOAc was added 200 mg of 10% Pd/C. The mixture was degassed, followed by addition of $H_2$ gas and stirred under an $H_2$ gas atmosphere for 2 h at RT. After filtration (celite), the product was concentrated and purified ($SiO_2$ chromatography, 5% EtOAc-hexanes) to give 857 mg (3.29 mmol) of 32 as a white solid (85% yield): TLC (5% EtOAc-hex) $R_f$ 0.7; $^1$ H-NMR ($CDCl_3$)δ 1.32 (s, 9H, $CH_3$), 1.42 (s, 9H, $CH_3$), 2.78 (t, J=6.0 Hz, 2H, $CH_2$), 4.52 (t, J=6.0 Hz, 2H, $CH_2$), 7.53 (d, J=2.4 Hz, 1H, Ar—H), 7.81 (d, J=2.4 Hz, 1H, Ar—H)

(6,8-Di-t-butylchroman-4-ylidene)acetonitrile (33) (trans) and (34) (cis). To 891 mg (5.03 mmol) of cyanomethyl phosphonate in 6 mL of dry THF was added 188 mg (4.69 mmol) of NaH (60% in oil) and the mixture was stirred for 20 min. To this solution was added 436 mg (1.80 mmol) of 32 in 2 mL of dry THF and the reaction was heated at reflux for 2 h. After cooling to RT, the reaction was quenched with saturated $NH_4Cl$ (10 mL) and extracted (2×10 mL EtOAc), washed (water, then brine), dried ($MgSO_4$), concentrated and purified ($SiO_2$ chromatography, 5% EtOAc-hexane) to give 358 mg (1.32 mmol) of the trans isomer 33 and 95 mg (0.35 mmol) of the cis isomer 34 (93% combined yield) Trans isomer 33,: TLC (5% EtOAc-hex) $R_f$ 0.5; $^1$H-NMR ($CDCl_3$)δ 1.30 (s, 9H, $3CH_3$), 1.36 (s, 9H, $3CH_3$), 3.00 (t, J=6.0 Hz, 2H, $CH_2$), 4.27 (t, J=6.0 Hz, 2H, $CH_2$), 5.73 (s, 1H, =CH—CN), 7.35 (d, J=2.4 Hz, 1H, Ar—H), 7.41 (d, J=2.4 Hz, 1H, Ar—H); Cis isomer 34: TLC (5% EtOAc-hex), $R_f$ 0.4; $^1$H-NMR ($CDCl_3$)δ 1.34 (s, 9H, $3CH_3$), 1.39 (s, 9H, $3CH_3$), 2.76 (t, J=6.0 Hz, 2H, $CH_2$), 4.29 (t, J=6.0 Hz, 2H, $CH_2$), 5.11 (s, 1H, =CH—CN), 7.42 (d, J=2 Hz, 1H, Ar—H), 8.28 (d, J=2 Hz, 1H, Ar—H).

(6,8-Di-t-butylchroman-4-ylidene)acetaldehyde (35) (trans). To 100 mg (0.36 mmol) of nitrile 33 in 5 mL of hexane at −78° C. was added 0.35 mL (0.53 mmol) of a 1.5 M solution of DIBAL in toluene. The mixture was stirred for 5 min. followed by addition of 10 mL of sat. aqueous Rochelle salt and warmed to RT. The solution was extracted (2×10 mL of EtOAc), washed (water then brine), dried ($MgSO_4$), filtered and concentrated to give 86 mg (0.30 mmol) of the relatively pure aldehyde 35 (83% yield): TLC (5% EtOAc-hex) $R_f$ 0.5, $^1$H-NMR ($CDCl_3$) δ 1.32 (s, 9H, $3CH_3$), 1.41 (s, 9H, $3CH_3$), 3.27 (t, J=6.0 Hz, 2H, $CH_2$), 4.30 (t, J=6.0 Hz, 2H, $CH_2$), 6.57 (d, J=8 Hz, 1H, =CH—CHO), 7.41 (d, J=2.4 Hz, 1H, Ar—H), 7.51 (d, J=2.4 Hz, 1H, Ar—H), 10.14 (d, J=8 Hz, 1H, CHO). (6,8-Di-t-butylchroman-4-ylidene) acetaldehyde (36) (cis). Compound 36 was prepared in the same manner as 35, except that the cis isomer 34 was used instead of 33: TLC (5% EtOAc-hex) $R_f$ 0.4, $^1$H-NMR ($CDCl_3$)δ 1.30 (s, 9H, $3CH_3$), 1.38 (s, 9H, $3CH_3$), 2.80 (t, J=6.5 Hz, 2H, $CH_2$), 4.42 (t, J=6.5 Hz, 2H, $CH_2$), 5.95 (d, J=8 Hz, 1H, =CH), 7.12 (d, J=2.4 Hz, 1H, Ar—H), 7.44 (d, J=2.4 Hz, 1H, Ar—H), 10.00 (d, J=8 Hz, 1H, CHO).

Ethyl (2E,4E,6E)-6-(6,8,-di-t-butylchroman-4-ylidene)-3-methylhexa-2,4,6-trienoate (37). To 238 mg (0.902 mmol) of triethyl-3-methyl-4-phosphonocrotonate in 3 mL of dry THF at −78° C. was added 0.36 mL (0.90 mmol) of a 2.5 M nBuLi solution in hexanes and 3 mL of DMPU.

After stirring for 15 min., the solution containing the ylide of triethylphosphonocrotonate was transferred to 86 mg (0.30 mmol) of 35 in 4 mL of 1:1 THF-DMPU at −78° C. The reaction mixture was warmed to RT, quenched with saturated aqueous $NH_4Cl$ (20 mL), and the products were extracted with EtOAc (2×20 mL). The extracts were washed (water then brine), dried ($MgSO_4$), filtered, concentrated and purified by column chromatography ($SiO_2$, 5% EtOAc-hexanes) to give 85.3 mg (0.22 mmol) of the 2E,4E,6E-isomer of 37 (73% yield) and 5.6 mg (0.014 mmol) of the 2Z,4E,6E isomer (5% yield). Compound 37: TLC (5% EtOAc-hex) $R_f$ 0.5, $^1$H-NMR ($CDCl_3$)δ 1.30 (t, J=7 Hz, 3H, $CH_2CH_3$), 1.33 (s, 9H, $3CH_3$), 1.37 (s, 91H, $3CH_3$), 2.37 (s, 3H, $CH_3$), 2.88 (t, J=6.0 Hz, 21H, $CH_2$), 4.17 (q, 2H, $CH_2$), 4.23 (t, J=6.0 Hz, 2H, $CH_2$), 5.81 (s, 1H, =CH), 6.43 (d, J=15 Hz, 1H, =CH), 6.73 (d, J=15 Hz, 1H, =CH), 6.96 (m, 1H, =CH), 7.25 (d, J=2.4 Hz, 1H, Ar—H), 7.50 (d, J=2.4 Hz, 1H, Ar—H).

Ethyl (2E,4E,6Z)-6-(6,8,-di-t-butylchroman-4-ylidene)-3-methylhexa-2,4,6-trienoate (38). Compound 38 was prepared in the same manner as 37 except that the cis isomer 36 was used instead of 35, Compound 36: TLC (5% EtOAc-hex) $R_f$ 0.5, $^1$H-NMR ($CDCl_3$)δ 1.30 (t, J=7 Hz, 3H, $CH_2CH_3$), 1.30 (s, 9H, $3CH_3$), 1.38 (s, 9H, $3CH_3$), 2.32 (s, 3H, $CH_3$), 2.66 (t, J=6.0 Hz, 2H, $CH_2$), 4.16 (m, 2H, $CH_2$), 4.35 (t, J=6.0 Hz, 2H, $CH_2$), 5.80 (s, 1H, =CH), 6.08 (d,J=11 Hz, 1H, =CH), 6.36 (d, J=15 Hz, 1H, =CH), 7.27 (d, J=2 Hz, 1 H, Ar—H), 7.29 (d, J=2 Hz, I H, Ar—H), 7.28 (dd, J=15, 11 Hz, 1H, Ar—H). (2E,4E, 6E)-6-(6,8,-Di-t-butylchroman-4-ylidene)-3-methylhexa-2,4,6-trienoic acid (39). To 85.3 mg (0.22 mmol) of ester 37 in 6 mL of 1:1 THF-MeOH was added 3 mL of an aqueous 5N KOH solution. The solution was heated at reflux for 10 min., cooled to RT, acidified (20% aqueous HCl) and extracted (2×6 mL of EtOAc). The extracts were combined, washed (water then brine), dried ($MgSO_4$), filtered and concentrated. Purification by preparative TLC (5% MeOH—$CHCl_3$), followed by crystallization (EtOAc-hexane, 1:4) gave 74.5 mg (0.20 mmol) of acid 39 as a pale yellow solid (94% yield): TLC (5% EtOAc-hex) $R_f$ 0.5; mp 237–239° C.; $^1$ H-NMR ($CDCl_3$)δ 1.33 (s, 9H, $3CH_3$), 1.38 (s, 9H, $3CH_3$), 2.37 (s, 3H, $CH_3$). 2.89 (t, J=6.0 Hz, 2H, $CH_2$), 4.23 (t, J=6.0 Hz, 2H, $CH_2$), 5.86 (s, 1H, =CH), 6.43 (d, J=15 Hz, 1H, =CH), 6.74 (d, J=11 Hz, 1H, =CH), 6.97 (dd, 11, 15 Hz, 1H, =CH), 7.25 (d, J=2.3 Hz, 1H, Ar—H), 7.50 (d, J=2.3 Hz, 1H, Ar—H).

(2E,4,6Z)-6-(6,8,-Di-t-butylchroman-4-ylidene)-3-methylhexa-2,4,6-trienoic acid (40). Compound 40 was prepared in the same manner as 39, except that the cis isomer 37 was used instead of 36, Compound 37: TLC (5% EtOAc-hex) $R_f$ 0.5; mp 233–235° C.; $^1$H-NMR ($CDCl_3$)δ 1.32 (s, 9H, $3CH_3$), 1.37 (s, 9H, $3CH_3$), 2.33 (s, 3H, $CH_3$). 2.68 (t, J=6.0 Hz, 2H, $CH_2$), 4.35 (t, J=6.0 Hz, 2H, $CH_2$), 5.83 (s, 1H, =CH), 6.10 (d, J=11 Hz, 1H, =CH), 6.39 (d, J=15 Hz, 1H, =CH), 7.26 (d, J=2 Hz, 1H, Ar—H), 7.30 (d, J=2 Hz, 1H, Ar—H), 7.35 (dd, J=11, 15 Hz, 1H, =CH).

EXAMPLE 9

(2E, 4E, 6E)-7-(3,5-Di-trifluoromethylphenyl)-3-methylocta-2,4,6-trienoic acid (41), prepared according to Scheme 1.

This compound was synthesized in an analogous manner as 9, except that 3,5-di-trifluoromethylacetophenone was used instead of 3,5-di-t-butylacetophenone: TLC (5% EtOAc-hex) $R_f$ 0.5; mp 225–227° C.; $^1$H-NMR ($CDCl_3$)δ 2.30 (s, 3H, $CH_3$). 2.40 (s, 3H, $CH_3$), 5.90 (s, 1H, =CH), 6.52 (d, J=15 Hz, 1H, =CH), 6.66 (d, J=12 Hz, 1H =CH), 7.03 (m, 1H, =CH), 7.78 (s, 1H, Ar—H), 7.87 (s, 1H, Ar—H).

EXAMPLE 10

(2E, 4E, 6E)-7-(3,5-Di-isopropylphenyl)-3-methylocta-2,4,6-trienoic acid (42), prepared according to Scheme 1.

This compound was synthesized in an analogous manner as 9, except that 3,5-di-isopropylacetophenone was used instead of 3,5-di-t-butylacetophenone: TLC (5% EtOAc-hex) $R_f$ 0.5; mp 157–160° C.; $^1$H-NMR ($CDCl_3$)δ 1.28 (d, J=8 Hz, 12 H, $CH_3$), 2.27 (s, 3H, $CH_3$). 2.42 (s, 3H, $CH_3$), 2.90 (p, J=8 Hz, 2H, CH), 5.83 (s, 1H, =CH), 6.42 (d, J=15 Hz, 1H, =CH), 6.60 (d, J=15 Hz, 1H=CH), 7.02 (s, 1H, Ar—H), 7.08 (m, 1H, =CH), 7.45 (s, 2H, Ar—H).

EXAMPLE 11

(2E, 4E, 6Z)-7-(3,5-Di-isopropylphenyl)-3-methylocta-2,4,6-trienoic acid (43), prepared according to Scheme 1.

This compound was synthesized in an analogous manner as 10, except that 3,5-di-isopropylacetophenone was used in the first step instead of 3,5-di-t-butylacetophenone: TLC (5% EtOAc-hex) $R_f$ 0.5; mp 177–179° C.; $^1$H-NMR ($CDCl_3$)δ 1.25 (d, J=7 Hz, 12 H, $CH_3$), 2.18 (s, 3H, $CH_3$). 2.21 (s, 3H, $CH_3$), 2.90 (p, J=7 Hz, 2H, CH), 5.77 (s, 1H, =CH), 6.25 (d, J=11 Hz, 1H, =CH), 6.27 (d, J=15 Hz, 1H=CH), 6.85 (dd, J=11, 15 Hz, 1H, Ar—H), 6.94 (d, J=2 Hz, 2H, Ar—H), 7.02 (bs, H, Ar—H).

EXAMPLE 12

(2E, 4E, 6E)-7-(4-T-butyl-phenyl)-3-methylocta-2,4,6-trienoic acid (44), prepared according to Scheme 1.

This compound was synthesized in an analogous manner as 9, except that 4-t-butylacetophenone was used instead of 3,5-di-t-butylacetophenone. TLC (5% EtOAc-hex) $R_f$ 0.5; mp 198–200° C.; $^1$H-NMR ($CDCl_3$)δ 1.33 (s, 9H, $3CH_3$), 2.26 (s, 3H, $CH_3$). 2.39 (s, 3H, $CH_3$). 5.84 (s, 1H, =CH), 6.40 (d, J=15 Hz, 1H, =CH), 6.60 (d, J=12 Hz, 1H=CH), 7.07 (m, 1H, =CH), 7.38 (s, 1H, Ar—H), 7.43 (s, 1H, Ar—H).

EXAMPLE 13

(2E, 4E, 6E)-7-(3,5-Di-t-butyl-4-methoxyphenyl)-3-methylocta-2,4,6-trienoic acid (45), prepared according to Scheme 1.

This compound was synthesized in an analogous manner as 9, except that 3,5-di-t-butyl-4-methoxyacetophenone was used instead of 3,5-di-t-butyl-acetophenone: TLC (5% EtOAc-hex) $R_f$ 0.5; mp 244–246° C.; $^1$H-NMR ($CDCl_3$)δ 1.30 (s, 9H, $3CH_3$), 1.42 (s, 9H, $3CH_3$), 2.27 (s, 3H, $CH_3$). 2.42 (s, 3H, $CH_3$), 3.67 (s, 3H, $OCH_3$), 5.83 (s, 1H, =CH), 6.34 (d., J=15 Hz, 1H, =CH), 6.35 (d, J=15 Hz, 1H=CH), 7.00 (d, J=2 Hz, 1H, Ar—H), 7.06 (m, 1H, =CH), 7.27 (d, J=2 Hz, 1H, Ar—H).

EXAMPLE 14

(2E, 4E, 6Z)-7-(3,5-Di-trifluoromethylphenyl)-3-methylocta-2,4,6-trienoic acid (46), prepared according to Scheme 1.

This compound was synthesized in an analogous manner as 10, except that 3,5-di-trifluoromethyl-acetophenone was used instead of 3,5-di-t-butyl-acetophenone. TLC (5% EtOAc-hex) $R_f$ 0.5; mp 225–227° C.; $^1$H-NMR (CDCl$_3$)δ 2.15 (s, 3H, CH$_3$), 2.24 (s, 3H, CH$_3$), 5.82 (s, 1H, CH=), 6.36 (d, J=5 Hz, 1H, CH=), 6.39 (d, J=9.7 Hz, 1H, CH=), 6.53 (dd, J=15 Hz, 9.7 Hz, 1H, CH=), 7.70 (s, 2H, Ar—CH), 7.83 (s, 1H, Ar—CH).

EXAMPLE 15

(2E, 4E, 6E) -3-Methyl-7-(3,5-di-t-butyl-4-methoxyphenyl) octa-2,4,6-trienoic acid (47), prepared according to Scheme 1.

This compound was synthesized in an analogous manner as 9, except that 3,5-di-t-butyl-4-methoxyacetophenone was used instead of 3,5-di-t-butylacetophenone: TLC (50% EtOAc-50% hexanes) $R_f$ 0.5; mp 213–216° C.; $^1$H-NMR (CDCl$_3$)δ 1.45 (s, 18H, 6(CH$_3$)), 2.25, (s, 3H, CH$_3$), 2.40 (s, 3H, CH$_3$),3.70 (S,3H . OCH$_3$), 5.84 (s, 1H, =CH), 6.41 (d, J=15 Hz, 1H, =CH), 6.52 (d,J=11.2 Hz, 1H, =CH), 7.08 (m, 1H, =CH), 7.35 (s, 2H, Ar—H).

EXAMPLE 16

(2E,4E,6E)-3-Methyl-7-(3,4-diethylphenyl)octa-2,4,6-trienoic acid (48), prepared according to Scheme 1.

This compound was synthesized in an analogous manner as 9, except that 3,4-di-ethylacetophenone was used instead of 3,5-di-t-butylacetophenone: TLC (20% EtOAc-80% hexanes) $R_f$ 0.3; mp 153–155° C.; $^1$H-NMR (CDCl$_3$)δ 1.45 (dd, J=14.1 Hz,7.5 Hz, 6H, 2CH$_3$), 2.25 (s,3H,CH$_3$), 2.39 (s, 3H, CH$_3$), 2.66 (m, 4H, 2CH$_2$), 5.83 (s, 1H, =CH), 6.40 (d, J=15 Hz, 1H, =CH), 6.59 (d, J=11.2 Hz, 1H, =CH), 7.07 (m, 1H, =CH), 7.14 (d, J=7.8 Hz, 1H, Ar—H), 7.27 (d, J=7.8 Hz, 1H, Ar—CH), 7.28 (s, 1H, Ar—CH).

EXAMPLE 17

(2E,4E,6Z)-3-Methyl-7-(3,4-di-ethylphenyl)octa-2,4,6-trienoic acid (49), prepared according to Scheme 1.

Compound 49 was prepared in the same manner as 10, except that 3,4-diethylacetophenone was used instead of 3,5-di-t-butylacetophenone: TLC (20% EtOAc-80% hexanes) $R_f$ 0.32; $^1$H-NMR (CDCl$_3$)δ 1.23 (dd, J=14.1 Hz,7.5 Hz, 6H, 2CH$_3$), 2.18 (s,6H,2CH$_3$), 2.67 (m, 4H, 2CH$_2$), 5.76 (s, 1H, =CH), 6.23(d, J=11.8 Hz, 1H, =CH), 6.28 (d, J=15 Hz, 1H, =CH), 6.83 (m, 1H, =CH), 7.04 (d, J=7.8 Hz, 1H, Ar—H), 7.06 (s, 1H, Ar—CH), 7.17 (d, J=7.8 Hz, 1H, Ar—CH).

EXAMPLE 18

(2E, 4E, 6E)-3-Methyl-7-(3,5-di-t-butyl-4-ethoxyphenyl) octa-2,4,6-trienoic acid (50), prepared according to Scheme 1.

This compound was synthesized in an analogous manner as 9, except that 3,5-di-t-butyl-4-ethoxyacetophenone was used instead of 3,5-di-t-butylacetophenone: TLC (50% EtOAc-50% hexanes) $R_f$ 0.5; mp 236–239° C.; $^1$H-NMR (CDCl$_3$)δ 1.41 (t, J=7.0 Hz, 3H, CH$_3$), 1.44 (s, 18H, 6(CH$_3$)), 2.26 (s, 3H, CH$_3$), 2.40 (s, 3H, CH$_3$), 3.77 (q, J=7 Hz, 2H . OCH$_2$CH$_3$), 5.84 (s, 1H, =CH), 6.41 (d, J=15 Hz, 1H,=CH), 6.51 (d,J=11.2 Hz, 1H, =CH), 7.08 (m, 1H, =CH), 7.35 (s, 2H, Ar—H).

EXAMPLE 19

(2E,4E,6E)-3-Methyl-7-(3,4-di-t-butylphenyl)octa-2,4,6-trienoic acid (51), prepared according to Scheme 1.

This compound was synthesized in an analogous manner as 9, except that 3,4-di-t-butylacetophenone was used instead of 3,5-di-t-butylacetophenone: TLC (20% EtOAc-80% hexanes) $R_f$ 0.3; mp 195–199° C.; $^1$H-NMR (CDCl$_3$) d 1.56 (s, 9H, 3CH$_3$), 1.58 (s, 9H, 3CH$_3$), 2.26 (s, 3H, CH$_3$), 2.40 (s, 3H, CH$_3$), 5.84 (s, 1H, =CH), 6.41 (d, J=15 Hz, 1H, =CH), 6.59 (d, J=11 Hz, 1H, =CH), 7.08 (m, 1H, =CH), 7.23 (dd, J=8.5, 2.3 Hz, 1H, Ar—H), 7.57 (d, J=8.5 Hz, 1H, Ar—H), 7.72 (d, J=2.3 Hz, 1H, Ar—H).

EXAMPLE 20

(2E,4E,6E)-3-Methyl-7-cyclohexyl-7-(3,5-di-t-butylphenyl)hepta-2,4,6-trienoic acid (52), prepared according to Scheme 4.

This compound was synthesized in an analogous manner as 27, except that 3,4-di-t-butylphenylcyclohexyl ketone was used instead of 3,5-di-t-butylbutan-1-one: TLC (20% EtOAc-80% hexanes) $R_f$ 0.3; $^1$H-NMR (CDCl$_3$) $^1$H NMR (CDCl$_3$)δ 1.35 (s, 9H), 1.9–1.1 (m,m, 8H), 2.40 (s, 3H), 2.85 (m, 1H), 5.81 (s, 1H), 6.08 (d, 1H, J=11.3 Hz), 6.30 (d, 1H, J=15.8 Hz), 7.02 (s, 2H, Ar—H), 7.14 (dd, 1H, J=15.2, 15.2 Hz), 7.33 (s, 1H, Ar—H),

EXAMPLE 21

(2E,4E,6E)-3-Methyl-7-(3,5-di-t-butylphenyl)nona-2,4,6-trienoic acid (53), prepared according to Scheme 1.

This compound was synthesized in an analogous manner as 9, except that 3,5-di-t-butyl-4-methoxyacetophenone was used instead of 3,5-di-t-butylacetophenone: TLC (50% EtOAc-50% hexanes) $R_f$ 0.5; mp 213–216° C.; $^1$H-NMR (CDCl$_3$)δ 1.45 (s, 18H, 6(CH$_3$)), 2.25, (s, 3H, CH$_3$), 2.40 (s, 3H, CH$_3$),3.70 (S,3H, OCH$_3$), 5.84 (s, 1H,=CH), 6.41 (d, J=15 Hz, 1H, =CH), 6.52 (d,J=11.2 Hz, 1H, =CH), 7.08 (m, 1H, =CH), 7.35 (s, 2H, Ar—H).

EXAMPLE 22

(2E,4E,6Z)-3-Methyl-7-(3,4-diethyl-6-methylphenyl)nona-2,4,6-trienoic acid (54), prepared according to Scheme 1.
This compound was synthesized in an analogous manner as 10, except that 3,4-diethyl-6-methylacetophenone was used instead of 3,5-di-t-butylacetophenone: TLC (20% EtOAc-80% hexanes) $R_f$ 0.3; $^1$H-NMR (CDCl$_3$)δ 1.22 (t, J=7.5 Hz, 3H, CH$_3$), 1.24 (t, J=7.5 Hz, 3H, CH$_3$), 2.08 (s, 3H, CH$_3$), 2.09 (s, 3H, CH$_3$), 2.17 (s, 3H, CH$_3$), 2.60 (m, 4H, 2(CH$_2$)), 5.73 (s, 1H, =CH), 6.25 (m, 3H, 3(=CH)), 6.81 (s, 1H, Ar—H), 7.01 (s, 1H, Ar—H).

EXAMPLE 23

(2E, 4E, 6E)-7-(3,5-Di-t-butylphenyl)-3-methylocta-2,4,6-trienoic acid (69), prepared according to Scheme 6 illustrated and described below.

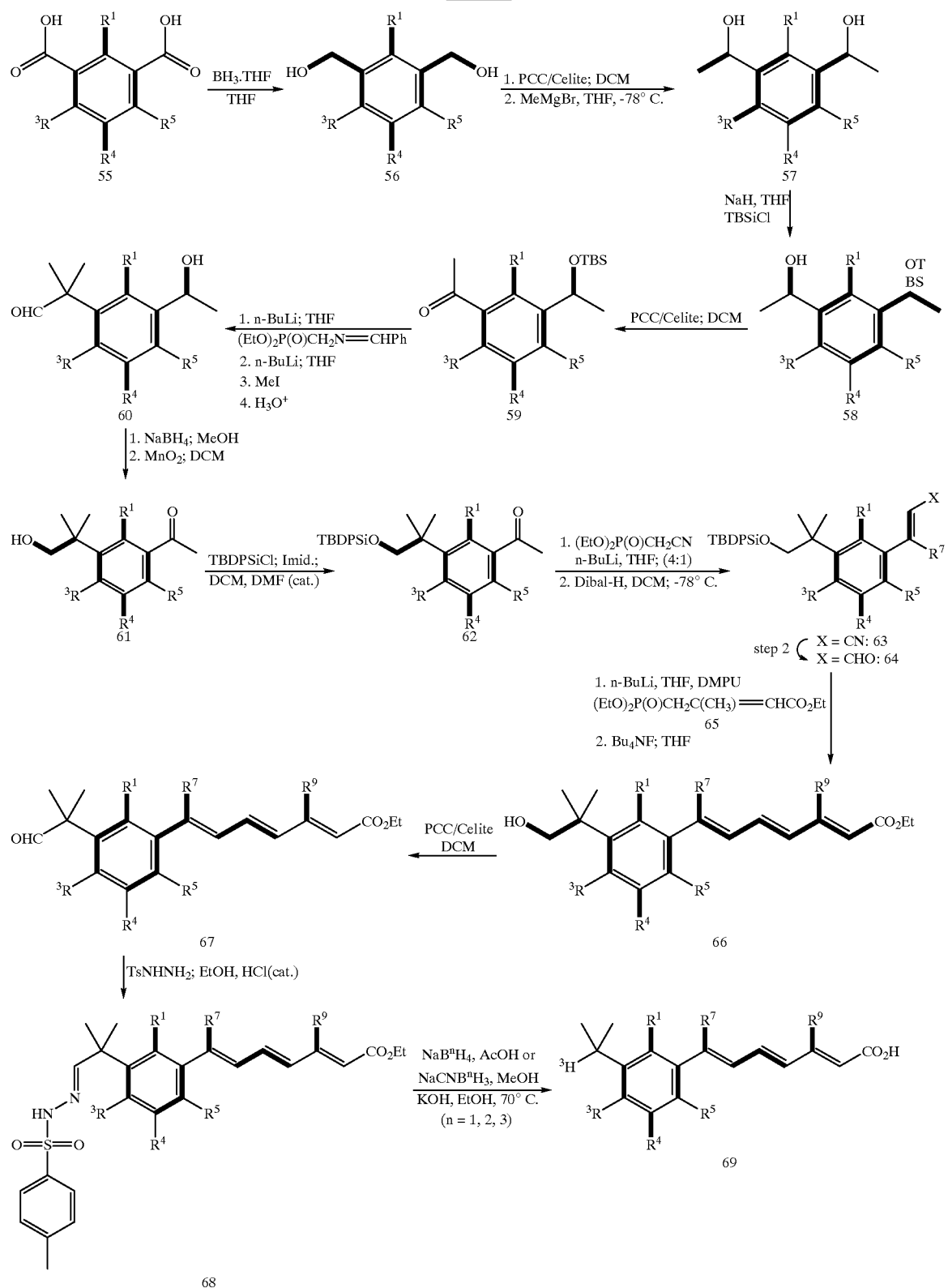
Scheme 6
5-tert-Butyl-1,3-benzene dimethanol (56). A solution of 5-tert-butyl-1,3-benzene dicarboxylic acid (55) 20.0 g (89.9 mmol) in THF (200 mL) was cooled at 0° C. and a solution of borane-THF complex in THF (190 mL) was slowly added via an addition funnel over 20 minutes with vigorous stirring. The mixture was warmed to RT and stirred for an additional 90 min. A mixture of water-THF (1:1; 200 mL) was slowly added, followed by an additional 200 mL of water. The mixture was extracted with ethyl acetate. The aqueous layer was extracted with EtOAc (2×100 mL) and the combined organic layers washed with water (2×100 mL); brine (2×100 mL) and dried over $MgSO_4$. The solvent was evaporated to give the pure diol in 98% yield: $^1H$ NMR ($CDCl_3$; 400 MHz)δ (ppm): 7.32 (s, 2H); 7.19 (s, 1H); 4.69 (s, 4H); 1.75 (br. s; 2H); 1.33 (s, 9H).

5-tert-Butyl-1,3-terephthaldehyde. 5-tert-Butyl-1,3-benzene dimethanol (56) (20.0 g; 103 mmol) was added to a vigorously stirring mixture of pyridinium chlorochromate (66.0 g; 306 mmol) and celite (130 g) in dichloromethane (DCM) (500 mL). The mixture was stirred for 3 h at RT until completion (TLC). The reaction mixture was filtered over a short pad of silica gel (2"×4") and eluted with DCM (1 L). The solvent was evaporated to give 18.7 g; 94% yield of the desired dialdehyde: $^1H$ NMR ($CDCl_3$; 400 MHz)δ (ppm): 10.11 (s, 2H); 8.18 (s, 3H); 1.41 (s 9H).

(R, S)-5-tert-Butyl-1,3-benzene-[2,2'-diethanol] (57). A solution of 5-tert-butyl-1,3-terephthaldehyde (18.7 g; 96.4 mmol) in THF (400 mL) was cooled to -78° C., and a solution of methyl magnesium bromide (80.0 mL of a 3 M solution) slowly added, and the reaction mixture was warmed to rt. After stirring for 60 min., the solution was quenched with a sat. $NH_4Cl$ solution (100 mL), followed by HCl (1 N, 50 mL) and extraction with EtOAc. The organic layer was washed with water (2×100 mL); brine (2×100 mL) and dried over $MgSO_4$. The solvent was evaporated. The crude residue was dissolved in hot EtOAc (30 mL) and pentane (200 mL) was added. The clear solution was cooled in a -4° C. refrigerator for 3 h. The white solid obtained was filtered and rinsed with cold pentane. The solid was dried in vaccuo to give 15.3 g (70% yield) of the desired compound: $^1H$ NMR ($CDCl_3$; 400 MHz)δ (ppm): 7.32 (s, 2H); 7.2 (s, 1H); 4.92 (m, 2H); 1.82 (d, 2 H, J=2.5 Hz); 1.52 (d, 6 H, J=6.5 Hz); 1.35 (s, 9H).

(R, S)-5-tert-Butyl-1,3-phenyl-[2-ethanol, 2'-ethane-tert-butyl dimethyl silyl ether] (58). Sodium hydride (2.75 g of a 60% mineral oil content mixture) was rinsed with hexanes (2×10 ml), suspended in THF (200 mL) and 5-tert-butyl-1,3-benzene-2,2'-diethanol (12.69 g; 57 mmol) was added with vigorous stirring. The mixture was stirred for 45 min. at rt to give a white slurry then tert-butyldimethylsilyl chloride (8.61 g, 57 mmol) was added at once. The reaction mixture was stirred for 2 h. and water (25 mL) was added. The mixture was extracted with EtOAc (350 mL). The organic layer was washed with a sat. $NH_4Cl$ solution (100 mL); water (2×100 mL); brine (2×100 mL) and dried over $MgSO_4$. The solvent was evaporated and the residue purified by flash chromatography over silica gel to give the desired monosilylated product (14.45 g; 75% yield) as an oil (2.14 g of the starting material was recovered): $^1H$ NMR ($CDCl_3$; 400 MHz)δ (ppm): 7.32 (s, 1H); 7.28 (s, 1H); 7.12 (2s, 1H); 4.92 (m, 2H); 1.85 (s, 1H); 1.5 (d, 3 H, J=6.5 Hz); 1.43 (d, 3 H, J=6.5 Hz) 1.35 (s, 9H); 0.9 (s, 9H); 0.05 (s, 6H).

(R, S)-3-(Ethyl-2-tert-butyldimethyl silyl ether)-5-tert-butylacetophenone (59). Pyridinium chlorochromate (15.0 g; 69 mmol) and celite (30 g) were mixed in DCM (500 mL) while 5-tert-butyl-1,3-benzene-(2-ethanol, 2'-ethane-tert-butyldimethyl silyl ether) (14.45 g; 44 mmol) in DCM (100 mL) was added with vigorous stirring. After 3 h at rt, the mixture was filtered over a short pad of silica gel (2"×4") and eluted with DCM (500 L). The solvent was evaporated to give the desired ketone (14.4 g, 99% yield). $^1H$ NMR ($CDCl_3$; 400 MHz)δ (ppm): 7.89 (s, 1 H); 7.73 (s, 1H); 7.65 (s, 1H); 4.94 (q, 1H, J=6.3 Hz); 2.63 (s, 3H); 1.45 (d, 3 H, J=6.3 Hz); 1.37 (s, 9H); 0.96 (s, 9H); 0.12 (s, 3H); -0.05 (s, 3H).

5-tert-Butyl-1-(2-ethanol)-3-(2-[2-methylpropan-1-al])-benzene (60). A flame-dried three-necked round bottom flask, was charged with THF (90 mL) and cooled to -78° C. n-BuLi (12.0 mL of a 2 M solution; 24 mmol) was slowly added and the mixture stirred for 10 min. A solution of N-benzylidene diethyl aminomethyl phosphonate (6.14 g; 24 mmol) in THF (15 mL) was added and the resulting mixture stirred for 60 min at -78° C. A solution of 5-tert-butyl-3-(ethane-2-tert-butyldimethylsilyl ether] acetophenone (7.0 g, 20.9 mmol) in THF (15 mL) was added to the above solution, and the mixture was warmed to room temp., stirred for 30 min., then refluxed for 2 h. The mixture was cooled to rt and the solvent was evaporated. Diethyl ether (400 mL) was added and the solution was washed with sodium chloride (200 mL). The aqueous layer was extracted with ether (200 mL) and the combined organic layers were washed with brine (200 mL) and dried over $MgSO_4$. The solvent was evaporated to give a yellow residue which was dried under high vaccuo (1 mm.Hg) for 1 hour. THF (90 mL) was added to this residue and cooled to -78° C. n-BuLi (12.0 mL of a 2 M solution; 24 mmol) was slowly added and the deeply colored solution was stirred for 60 min. Methyl iodide (6.52 mL) was added and the mixture was warmed to room temperature and stirred for 4 h. The reaction mixture was quenched with HCl (3 N; 100 mL) and the biphasic solution was stirred for 16 h at RT. EtOAc (300 mL) was added and the organic layer was separated and washed with water (2×100 mL), brine (2×100 mL), and dried over $MgSO_4$. The solvent was evaporated to give a residue which was purified by s.g.c. to give 3.3 g of the desired aldehyde in 65% yield: $^1H$ NMR ($CDCl_3$; 400 MHz)δ (ppm): 9.5 (s, 1H); 7.33 (s, 1H); 7.17 (s, 1H); 7.11 (s, 1H); 4.91 (m, 1H); 1.80 (d, 1 H, J=3.4 Hz); 1.5 (d, 3 H, J-6.3 Hz); 1.47 (s, 3H); 1.32 (s, 9H).

5-tert-Butyl-3-(2-methylpropan-1-ol]acetophenone (61). A solution of 5-tert-butyl-1-(2-ethanol)-3-(2-[2-methylpropan-1-al])benzene (1.77 g, 7.53 mmol) in MeOH (50 mL) was cooled to 0° C. and $NaBH_4$ (300 mg, 7.93 mmol) was added portionwise. The reaction mixture was warmed to RT and stirred for 30 min. The solvent was evaporated and the residue taken up in EtOAc (50 mL) and washed with HCl (10%, 3×10 mL); water (3×20 mL) and brine (3×20 mL). The organic layer was dried over $MgSO_4$ and evaporated to dryness to give the desired diol 1.76 g; 99% yield. This diol (1.65 g; 6.78 mmol) was dissolved in DCM (20 mL) and $MnO_2$ (18.7 g; 0.17 mmol) was added at once. The reaction mixture was vigorously stirred for 4 h, then filtered over a short pad of celite. The solvent was evaporated to give 1.63 g (97% yield) of the desired ketone: $^1H$ NMR ($CDCl_3$; 400 MHz)δ (ppm): 7.85 (s, 1H); 7.8 (s, 1H); 7.63 (s, 1H); 3.64 (d; 2 H, J=4.5 Hz); 2.6 (s, 3H); 1.38 (s, 6H); 1.35 (s, 9H).

5-tert-Butyl-3-(2-[2-methylpropan-1-tert-butyldiphenylsilylether])acetophenone (62). To a solution of 5-tert-butyl-3-(2-methylpropan-1-ol]acetophenone (1.63 g; 6.96 mmol) in DCM (30 mL) was added imidazole (500 mg; 7.35 mmol), a drop of DMF and tert-butyldiphenylsilyl chloride (2.01 g; 7.33 mmol). The mixture was stirred overnight at RT and quenched with excess sat. NH₄Cl. DCM (50 mL) was added and the organic layer washed with water (3×20 mL) and brine (3×20 mL). The organic layer was dried over MgSO₄ and evaporated to dryness to give a residue which was purified by s.g.c. to give the desired ether 2.77 g (83% yield): $^1$H NMR (CDCl₃; 400 MHz)δ (ppm): 7.85 (s, 1H), 7.76 (s, 1H); 7.63 (1H); 7.48–7.25 (mm, 10 H); 3.62 (s, 2H); 2.56 (s, 3H); 1.38 (s, 6H); 1.33 (s, 9H); 0.94 (s, 9H).

5-tert-Butyl-3-(2-[2-methylpropan-1-tert-butyldiphenylsilylether])-1-(2E)-3–12-butenitrile)-benzene (63). To a solution of diethyl cyanomethyl phosphonate (1.7 g, 9.55 mmol) in THF (30 mL) at 0° C. was added n-BuLi (4.64 mL of a 2.0 M solution in hexanes). The solution was stirred for 10 min., after which a solution of 5-tert-butyl-3-(2-[2,2'-dimethylpropan-tert-butyldiphenylsilyl ether])acetophenone in THF (10 mL) was added. The reaction mixture was stirred for 30 min. and quenched with a sat. NH₄Cl solution. EtOAc (50 mL) was added and the organic layer was washed with water (3×20 mL) and brine (3×20 mL). The organic layer was dried over MgSO₄ and evaporated to dryness to give a residue which was purified by s.g.c. to give the desired nitrile as a trans:cis mixture (~4:1 by $^1$H NMR). S.g.c. gave the desired trans isomer 1.70 g, 63% yield: $^1$H NMR (CDCl₃; 400 MHz)δ (ppm): 7.85 (s, 1H), 7.48–7.22 (mm, 13 H, ArH); 5.5 (s, 1H); 3.59 (s, 2H); 2.43 (s, 3H); 1.35 (s, 6H); 1.27 9s, 9H); 0.94 (s, 9H).

5-tert-Butyl-3-(2-[2-methylpropan-1-tert-butyldiphenylsilylether])-1-(2E)-(3-[2-butenal)benzene (64). A solution of 5-tert-butyl-3-(2-[2-methylpropan-1-tert-butyldiphenylsilylether])-1-(3-[3-methyl-2-propenitrile)benzene (1.7 g; 3.42 mmol) in anhydrous DCM (20 mL) was cooled to −78° C. and Dibal (3.5 mL of a 1 M solution in toluene) was added dropwise. The reaction mixture was stirred at −78° C. for 60 min, quenched with excess Rochelle salt, then allowed to warm to RT. EtOAc (50 mL) was added and the mixture washed with water (3×20 mL) and brine (3×20 mL). The organic layer was dried over MgSO₄ and evaporated to dryness to give a residue which was purified by s.g.c. to give 1.25 g of the desired aldehyde (74% yield): $^1$H NMR (CDCl₃; 400 MHz)δ (ppm): 10.17 (d, 1 H; J=8 Hz); 7.48–7.22 (mm, 13 H, ArH); 6.36 (d, 1 H, J=8 Hz); 3.60 (s, 2H); 2.54 (s, 3H); 1.37 (s, 6H); 1.32 (s, 9H); 0.94 (s, 9H).

Ethyl-(2E, 4E, 6E)-7-(5-tert-butyl-3-[2-(2-methylpropan-1-ol]-1'-benzene)-3-methylocta-2,4,6-trienoate (66). A solution of diethyl 3-ethoxycarbonyl-2-methylprop-2-enyl phosphonate (1.20 g, 4.52 mmol) in anhydrous THF (20.0 mL) was cooled to 0° C. and added with anhydrous DMPU (3.5 mL) and n-BuLi in hexanes (2.15 mL of 2.o M solution, 4.50 mmol). The mixture was stirred at this temperature for 20 min., then cooled to −78° C. A solution of 5-tert-butyl-3-(2-[2-methyl propane-1-tert-butyldiphenylsilyl ether])-1-(3-[3-methyl-2-propenal)benzene (1.25 g, 2.52 mmol) in THF (10.0 mL) was slowly added and the reaction mixture stirred at −78° C. for an additional 60 min. The mixture was allowed to warm to 23° C. for 1 h with stirring. A sat. solution of ammonium chloride (5 mL) was added and the mixture extracted using EtOAc (3×10 mL). The organic layer was with water (2×25 mL) and brine (50 mL), dried over MgSO₄ and concentrated. The reidue was purified on a short sgc column to give 1.35 g (86% yield) of the desired ester (65). The above silyl ether (1.05 g, 1.68 mmol) was dissolved in THF (20 mL) and tetrabutylammonium fluoride (17 mL of 1 M solution in THF) was added. The reaction mixture was stirred at room temperature for 12 h, and EtOAc (50 mL) was added, followed by wash with water (2×20 mL), brine (20 mL). The organic layer was separated, dried over MgSO₄ and evaporated to dryness. The residue was purified by s.g.c. to give 479 mg (80% yield) of the desired alcohol: $^1$H NMR (CDCl₃; 400 MHz)δ (ppm): 7.9 (d, 1H; J=16 Hz, 2:cis isomer; ~15%); 7.34 (s, 2H), 7.29 (s, 1H), 7.03 (dd, 1H, J=16 Hz); 6.53 (d, 1H, J=12 Hz); 6.38 (d, 1 H, J=16 Hz); 5.72 (s, 1H); 5.68 (s, 1H, 2:cis isomer; ~15%); 4.15 (q, 2 H, J=6.7 Hz); 3.62 (s 2H); 2.38 (s, 3H); 2.28 (s, 3H); 1.6 (br. s; 1H); 1.37 (s, 6H); 1.33 (s, 9H), 1.26 (t, 3 H, J=6.7 Hz).

Ethyl-(2E, 4E, 6E)-7-(5-tert-butyl-3-[2-(2-methylpropan-1-al)]-1'-phenyl)-3-methylocta-2,4,6-trienoate (67). To a vigorously stirred mixture of pyridinium chlorochromate (350 mg; 1.39 mmol) and celite (750 mg) in DCM (20 mL) was added a solution of ethyl-(2E, 4E, 6E)-7-(5-tert-butyl-3-[2-(2-methylpropan-1-ol)]-1'-phenyl)-3-methylocta-2,4,6-trienoate (330 mg; 0.889 mmol) in DCM (10 mL). The mixture was stirred for 3 h at rt and filtered over a short pad of silica gel. The solvent was evaporated and the residue purified by s.g.c. to give the desired aldehyde 290 mg (87% yield): $^1$H NMR (CDCl₃; 400 MHz)δ (ppm): 9.5 (s, 1H); 7.9 (d, 1H; J=16 Hz, 2:cis isomer; -15%); 7.34 (s, 2H), 7.29 (s, 1H), 7.03 (dd, 1 H, J=16 Hz); 6.53 (d, 1H, J=12 Hz); 6.38 (d, 1H, J=16 Hz); 5.79 (s, 1H); 5.68 (s, 1H, 2:cis isomer; ~15%); 4.15 (q, 2 H, J=6.7 Hz); 3.62 (s 2H); 2.38 (s, 3H); 2.28 (s, 3H); 1.37 (s, 6H); 1.33 (s, 9H), 1.26 (t, 3 H, J=6.7 Hz).

Ethyl-(2E, 4E, 6E)-7-(5-tert-butyl-3-[2-(2-methylpropan-1-al)]-1'-phenyl)-3-methylocta-2,4,6-trienoate p-toluenesulfonyl hydrazone (68). To a solution of ethyl-(2E, 4E, 6E)-7-(5-tert-butyl-3-[2-(2-methyl propanal)]-1'-phenyl)-3-methylocta-2,4,6-trienoate (250 mg, 0.67 mmol) in ethanol (5 mL) was added p-toluenesulfonyl hydrazide (137 mg, 0.73 mmol) and ~10 ml of conc. HCl. The mixture was heated at 40–45° C. for 15 min. The solvent was evaporated and the residue purified by s. g. c. to give 330 mg (89% yield): $^1$H NMR (CDCl₃; 400 MHz)δ (ppm): 7.82 (d, 2 H, J=7.4 Hz); 7.5 (2s, 2H); 7.3 (d, 2 H, J=7.4 Hz); 7.18 (s, 1H); 7.05 (s, 1H); 7.0 (dd, 1H, J=16 Hz); 6.45 (d, 1H, J=12 Hz); 6.38 (d, 1H, J=12 Hz); 5.82 (s, 1H); 4.2 (q, 2 H, J=6.7 Hz); 3.62 (s 2H); 2.42 (s, 3H); 2.38 (s, 3H); 2.28 (s, 3H); 1.37 (s, 6H); 1.33 (s, 9H), 1.26 (t, 3 H, J=6.7 Hz).

(2E, 4E, 6E)-7-(3,5-Di-tert-butylphenyl)-3-methylocta-2,4,6-trienoic acid (69)**. To a solution of ethyl-(2E, 4E, 6E)-7-(5-tert-butyl-3-[2-(2-methylpropan-1-al)]-1'-phenyl)-3-methylocta-2,4,6-trienoate p-toluenesulfonyl hydrazone (68) (80 mg) in acetic acid (2.0 mL) was added sodium borohydride* (80 mg) in small portions. The mixture was heated at 50° C. for 1 h, cooled to RT and added to ice; allowed to warm to ambient temperature and extracted with EtOAc (3×10 mL). The organic layer was washed with water (3×10 mL); NaHCO₃ (2×10 mL); water (3×10 mL); brine (3×10 mL); dried over MgSO₄ and evaporated. The residue was purified by s.g.c. to give the desired ester. This ester (20 mg) was dissolved in EtOH and KOH 1 M (1 mL) was added and the mixture heated at reflux for 3 h. The reaction mixture was cooled to RT; neutralized with HCl (10%) and extracted with EtOAc. The organic layer was washed with water (3×10 mL); brine (3×10 mL); dried over MgSO₄ and evaporated to give the desired acid. *Those skilled in the art will recognize that the above protocol can be adapted to use labeled and radiolabeled NaB"H₄ (n=1, 2, 3) to generate the labeled (i.e., tritium labeled) compounds shown in Scheme 6. **Furthermore, those skilled in the art will also recognize that the same labeled (deuterio and tritio)-compound (69) can be obtained from hyrazone (68) with heating for 8 h in methanol in the presence of NaCNB″H$_3$ (n=1, 2, 3) and ZnCl$_2$, followed by saponification (KOH, EtOH). In another alternative embodiment, aldehyde (67) is reduced with radiolabeled NaB″H$_4$ (n=1, 2, 3), and the resulting alcohol is then oxidized to the corresponding tritiated aldehyde. Conversion of such an aldehyde to its tosyl hydrazone, followed by reduction with sodium cyanoborohydride and ZnCl$_2$ in methanol, and saponification yields the corresponding acid (See 68 to 69 of Scheme 6.

Evaluation of Retinoid Receptor Subfamily Activity

Utilizing the "cis-trans" or "co-transfection" assay described by Evans et al., Science, 240:889–95 (May 13, 1988), the disclosure of which is herein incorporated by reference, the retinoid compounds of the present invention were tested and found to have strong, specific activity as either selective RAR agonists, selective RXR agonists, or as pan-agonist activators of both RAR and RXR receptors. This assay is described in further detail in U.S. Pat. Nos. 4,981,784 and 5,071,773, the disclosures of which are incorporated herein by reference.

The co-transfection assay provides a method for identifying functional agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human RARα, RARβ, RXRγ) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), is controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., all-trans retinoic acid for RARα) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of the retinoid compounds of the present invention were evaluated utilizing the co-transfection assay according to the following illustrative Example 23.

EXAMPLE 23

Co-transfection assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine RAR and/or RXR agonist activity of the compounds of the present invention, the CV-1 cells were transiently transfected by calcium phosphate coprecipitation according to the procedure of Berger et al., 41 *J. Steroid Biochem. Mol. Biol.,* 733 (1992) with the following receptor expressing plasmids: pRShRARα: Giguere et al., 330 *Nature,* 624 (1987); pRShRARβ and pRShRARγ, Ishikawa et al., 4 *Mol. Endocrin.,* 837 (1990); pRShRXRα, Mangelsdorf et al., 345 *Nature,* 224 (1990); and pRSmRXRβ and pRSmRXRγ, Mangelsdorf et al., 6 *Genes & Devel.,* 329 (1992), the disclosures of which are herein incorporated by reference. Each of these receptor expressing plasmids was co-transfected at a concentration of 5 ng/well, along with a basal reporter plasmid at 100 ng/well, the internal control plasmid pRS-β-Gal at 50 ng/well and filler DNA, pGEM at 45 ng/well.

The basal reporter plasmid D-MTV-LUC (Hollenberg and Evans, 55 *Cell,* 899 (1988), the disclosure of which is herein incorporated by reference) containing two copies of the TRE-palindromic response element described in Umesono et al., 336 *Nature,* 262 (1988), the disclosure of which is herein incorporated by reference, was used in transfections for the RARs, and the reporter plasmid CRBPIIFKLUC, which contains an RXRE (retinoid X receptor response element, as described in Mangelsdorf et al., 66 *Cell,* 555 (1991), the disclosure of which is herein incorporated by reference), was used in transfections for the RXRs. Each of these reporter plasmids contains the cDNA for firefly luciferase (LUC) under constitutive promoter containing the appropriate RAR or RXR response element. As noted above, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing compounds of the present invention in concentrations ranging from $10^{-12}$ to $10^{-5}$ M were added to the cells. Similarly, the reference compounds all-trans retinoic acid (ATRA)(Sigma Chemical), a known RAR selective compound, and 9-cis retinoic acid (9-cis) (synthesized as described in Heyman et al., *Cell,* 68:397–406 (1992)), a compound with known activity on RXRs, were added at similar concentrations to provide a reference point for analysis of the activity of the compounds of the present invention. Retinoid purity was established as greater than 99% by reverse phase high-performance liquid chromatography. Retinoids were dissolved in dimethylsulfoxide for use in the transcriptional activation assays. Three to four replicates were used for each sample.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal . ×10$^{-5}$/β-Gal incubation time.

The mean and standard error of the mean (SEM) of the NR were calculated. Data was plotted as the response of the compound compared to the reference compounds over the range of the dose-response curve. For the agonist compounds of the present invention, the effective concentration that produced 50% of the maximum response (EC$_{50}$) was quantified.

The potency (nM) of selected retinoid compounds of the present invention are in Table 1 below.

Table 1: Potency (nM) of selected retinoid compounds of the present invention on RARα,β,γ and RXRα,β,γ, in comparison to the known RAR-active retinoid compound all-trans retinoic acid (ATRA) and RXR-active retinoid compound 9-cis retinoic acid (9-cis), and in comparison to comparative example compounds A, B, C and D.

| Cmpd. No. | RARα Pot nM | RARβ Pot nM | RARγ Pot nM | RXRα Pot nM | RXRβ Pot nM | RXRγ Pot nM |
|---|---|---|---|---|---|---|
| 9 | 4 | 1 | <1 | na | na | na |
| 19 | 59 | 23 | 16 | 127 | 48 | 56 |
| 28 | na | na | na | 20 | 104 | 50 |
| 39 | 5 | 3 | 3 | na | na | na |
| 41 | 3 | 1 | 4 | 2007 | 266 | 2183 |
| 43 | 65 | 22 | 16 | 27 | 27 | 19 |
| 44 | 223 | 37 | 33 | 1443 | 21 | 224 |
| 47 | na | 1 | 1 | na | na | na |
| 54 | na | 130 | 320 | 58 | 28 | 78 |
| ATRA | 436 | 78 | 19 | 1015 | 1211 | 961 |
| 9-cis | 220 | 29 | 50 | 195 | 128 | 124 |
| A | na | 1484 | na | na | na | na |
| B | na | na | na | na | na | na |
| C | na | na | na | na | na | na |
| D | na | na | na | na | na | na | na = not active (potency of >10,000 and/or efficacy of <20%)

As can been seen in Table 1, Compounds 9, 39, 41 and 47 are extremely potent RAR active compounds, with Compound 9 displaying sub-nanomolar activity on RARγ, and Compound 47 displaying selectivity on RARβ and RARγ. In fact, these Compounds are 10 to over 100 times more potent than the known RAR active compound ATRA on the RARs. Likewise, Compound 28 is a very potent and selective RXR active compound. Furthermore, pan-agonist Compounds 10 and 43 display a superior potency profile to that of the known RXR active pan-agonist compound 9-cis retinoic acid. While efficacy is not reported in Table 1, those compounds displaying an efficacy of less than 20 percent are considered to be inactive as retinoid activators (potency defined as >10,000), even if the compounds display marginal potency. In this regard, except for comparative compound A on RARβ, the comparative example compounds all displayed efficacies of less than 20 percent.

The retinoid activity of the compounds of the present invention for RAR and/or RXR receptors is not exhibited by other known structurally similar compounds. As further shown in Table 1, comparative example compounds that appear structurally similar to the compounds of the present invention, such as (2E,4E,6E)-3-methyl-7-(3,4-dimethoxyphenyl)octa-2,4,6-trienoic acid (A) and (2E,4E,6E)-3-methyl-7-(4-methoxyphenyl)octa-2,4,6-trienoic acid (B) described in M. J. Aurell, et al., 49 Tetrahedron, 6089 (1993) (Scheme 2, compounds d and e), (2E,4E,6E)-2-methyl-7-(2,3,6-trimethyl-4-methoxyphenyl)hepta-2,4,6-trienoic acid (C) disclosed in U.S. Pat. No. 4,534,979 (Example 17), and (2E,4E,6E)-3-methoxy-7-(4-t-butylphenyl)octa-2,4,6-trienoic acid (D) disclosed in U.S. Pat. No. 5,320,833 (Compound 80), have no, or virtually no, activity on any of the RARs or RXRs.

EXAMPLE 24

In addition to the cotransfection data of Example 15, the binding of selected compounds of the present invention to the RAR and RXR receptors was also investigated according to the methodology described in M. F., Boehm, et al., "Synthesis and Structure-Activity Relationships of Novel Retinoid X Receptor Selective Retinoids", 37 *J. Med. Chem.*, 2930(1994); M. F. Boehm, et al., "Synthesis of High Specific Activity [$^3$H]-9-cis Retinoic Acid and Its Application for Identifying Retinoids with Unusual Binding Properties", 37 *J. Med. Chem.*, 408 (1994), and E. A. Allegretto, et al., "Characterization and Comparison of Hormone-Binding and Transactivation Properties of Retinoic Acid and Retinoid X Receptors Expressed in Mammalian Cells and Yeast", 268 *J. Biol. Chem.*, 22625 (1993), the disclosures of which are herein incorporated by reference.

Non-specific binding was defined as that binding remaining in the presence of 500 nM of the appropriate unlabelled compound. At the end of the incubation period, bound from free ligand were separated. The amount of bound tritiated retinoids was determined by liquid scintillation counting of an aliquot (700 mL) of the supernatant fluid or the hydroxylapatite pellet.

After correcting for non-specific binding, IC$_{50}$ values were determined. The IC$_{50}$ value is defined as the concentration of competing ligand needed to reduce specific binding by 50%. The IC$_{50}$ value was determined graphically from a log-logit plot of the data. The K$_i$ values were determined by application of the Cheng-Prussof equation to the IC$_{50}$ values, the labeled ligand concentration and the K$_d$ of the labeled ligand.

The binding activity (Kd in nM) results of selected retinoid compounds of present invention, and the reference compounds ATRA, and 9-cis RA, is shown in Table 2 below.
Table 2: Binding (Kd in nM) of selected retinoid compounds of the present invention on RARα,β,γ and RXRα,β,γ proteins in comparison to the known RAR-active retinoid compound all-trans retinoic acid (ATRA) and RXR-active retinoid compound 9-cis retinoic acid (9-cis).

| Cmpd. No. | RARα Binding K$_d$ (nM) | RARβ Binding K$_d$ (nM) | RARγ Binding K$_d$ (nM) | RXRα Binding K$_d$ (nM) | RXRβ Binding K$_d$ (nM) | RXRγ Binding K$_d$ (nM) |
|---|---|---|---|---|---|---|
| 9 | 1 | 2 | 4 | 270 | 924 | 496 |
| 10 | 59 | 75 | 121 | 4 | 4 | 9 |
| ATRA | 15 | 17 | 17 | 53 | 306 | 306 |
| 9-cis | 93 | 97 | 148 | 8 | 15 | 14 |

As can be seen in Table 2, Compounds 9 and 10 of the present invention show equal or superior binding to the known RAR active compound ATRA, and the known RXR active compound 9-cis. In comparison, all of the comparative example compounds of Example 14 show absolutely no binding on any of the retinoid receptors, with the exception of comparative example compound A, which shows weak binding of 312 nM on RARα.

EXAMPLE 25

Yet another recognized measure of the retinoid activity of the compounds of the present invention is the ornithine decarboxylase assay, as originally described by Verma and Boutwell, 37 *Cancer Research*, 2196 (1977), the disclosure of which is herein incorporated by reference. In Verma & Boutwell original work using retinoic acid, it was established that ornithine decarboxylase (ODC) activity increased in relation to polyamine biosynthesis. In turn, it had previously been established that increases in polyamine biosynthesis is correlated with cellular proliferation. Thus, if ODC activity could be inhibited, cell hyperproliferation could be modulated. Although all causes of increased OCD activity are yet unknown, it is known that 12—O—tetradecanoylphorbor-13-acetate (TPA) induces ODC activity. Importantly, retinoic acid inhibits this induction of ODC by TPA.

An ODC assay essentially following the procedures set out in 35 *Cancer Research*, 1662 (1975), the disclosure of which is herein incorporated by reference, was used to demonstrate the inhibition of TPA induction of ODC by the compounds of the present invention. The results of this assay on selected Example Compounds, and the reference compounds ATRA and (E)-4-[2-(5,6,7,8-tetrahydro-5,5,8,8-tetramethyl-2-napthalenyl)-1-propenyl]benzoic acid (TTNPB), known RAR active compounds, are shown below in Table 3. All values are expressed as the concentration of the indicated compounds in nM required to inhibit the TPA induction of ODC by 80 percent, i.e., the IC-80 in nM.

Table 3: Inhibitory concentration required to inhibit 80% of the maximally observed TPA induction of ODC (ODC $IC_{80}$) in nM for Compounds 7,8,9 and 10, and reference compounds ATRA and TTNBP.

| Compound | ODC $IC_{80}$ (nM) |
| --- | --- |
| 7 | 4.73 |
| 8 | 152 |
| 9 | 0.93 |
| 10 | 6.62 |
| ATRA | 1.40 |
| TTNPB | 0.09 |

Compounds 7 and 8, which are the esters of Compounds 9 and 10 respectively, have been included to show that such ester analogs exhibit retinoid activity. While not being bound to a theory of operation, it is believed that such esters may operate as pro-drugs in vivo, possibly due to the cleavage of the ester to the active acid form of the compounds of the present invention.

EXAMPLE 26

The in vitro affect of selected compounds of the present invention on the recognized cancer cell lines, RPMI 8226, ME 180 and AML-193, obtained from the American Type Culture Collection (ATCC, Rockville, Md.), was investigated.

RPMI 8226 is a human hematopoietic cell line obtained from the peripheral blood of a patient with multiple myeloma, and as such is a recognized model for multiple myelomas and related malignancies. Y. Matsuoka, G. E. Moore, Y. Yagi and D. Pressman, "Production of free light chains of immunoglobulin by a hematopoietic cell line derived from a patient with multiple myeloma", 125 *Proc. Soc. Exp. Biol. Med.*, 1246 (1967), the disclosure of which is herein incorporated by reference. The cells resemble the lymphoblastoid cells of other human lymphocyte cell lines and secretes X-type light chains of immunoglobulin. RPMI 83226 cells were grown in RPMI medium (Gibco) supplemented with 10% fetal bovine serum, glutamine and antibiotics. The cells were maintained as suspension cultures grown at 37° C. in a humidified atmosphere of 5% $CO_2$ in air. The cells were diluted to a concentration of $1 \times 10^5$/mL twice a week.

ME 180 is a human epidermoid carcinoma cell line derived from the cervix, and as such is a recognized model for squamous cell carcinomas and related malignancies. J. A. Sykes, J. Whitescarver, P. Jermstrom, J. F. Nolan and P. Byatt, "Some properties of a new epithelial cell line of human origin", 45 *MH-Adenoviridae J. Natl. Cancer Inst.*, 107 (1970), the disclosure of which is herein incorporated by reference. The tumor was a highly invasive squamous cell carcinoma with irregular cell clusters and no significant keratinization. ME 180 cells were grown and maintained in McCoy's 5a medium (Gibco) supplemented with 10% fetal bovine serum, glutamine and antibiotics. The cells were maintained as monolayer cultures grown at 37° C. in a humidified atmosphere of 5% $CO_2$ in air.

The AML-193 cell line was established from the blast cells of a patient with leukemia and was classified as M5 Acute Monocytic Leukemia, and as such is a recognized model for leukemias and related malignancies. G. Rovera, et al., 139 *J. Immunol.*, 3348 (1987), the disclosure of which is herein incorporated by reference. Over 75% of these cells are positive by immunofluorescence for the myelomonocytic antigen CS 15. The cells were grown in Iscove's modified Dulbeccos's medium with 5 µg/mL transferring, 5 gg/mL insulin and 2 ng/mL rh GM-CSF. The cells were maintained as suspension cultures grown at 37° C. in a humidified atmosphere of 5% $CO_2$ in air. The cells were diluted to a concentration of $1 \times 10^5$/mL twice a week.

Incorporation of $^3$H-Thymidine

Measurement of the level of radiolabeled thymidine incorporated into the above-identified cell lines provides a direct measurement of the antiproliferative properties of the compounds of the present invention. The method used for determination of the incorporation of radiolabeled thymidine was adapted from the procedure described by S. Shrivastav et al., "An in vitro assay procedure to test chemotherapeutic drugs on cells from human solid tumors", 40 *Cancer Res.*, 4438 (1980), the disclosure of which is herein incorporated by reference. RPMI 8226 or AML-193 cells were plated in a 96 well round bottom microtiter plate (Costar) at a density of 1,000 cells/well. To appropriate wells, retinoid test compounds were added at the final concentrations indicated for a final volume of 150 µL/well. The plates were incubated for 96 hours at 37° C. in a humidified atmosphere of 5% $CO_2$ in air. Subsequently, 1 µCi of [5'-$^3$H]-thymidine (Amersham, U.K, 43 Ci/mmol specific activity) in 25 µL culture medium was added to each well and the cells were incubated for an additional six hours. The cultures were further processed as described below.

ME 180 cells, harvested by trypsinization were plated in a 96 well flat bottom microtiter late (Costar) at a density of 2,000 cells/well. The cultures were treated as described above for RPMI 8226 with the following exceptions. After incubation, the supernatant was carefully removed, and the cells were washed with a 0.5 mM solution of thymidine in phosphate buffered saline. ME 180 cells were briefly treated with 50 µL of 2.5% trypsin to dislodge the cells from the plate. Both cell lines were then processed as follows: the cellular DNA was precipitated with 10% trichloroacetic acid onto glass fiber filter mats using a SKATRON multi-well cell harvester (Skatron Instruments, Sterling Va.). Radioactivity incorporated into DNA, as a direct measurement of cell growth, was measured by liquid scintillation counting. The mean disintegrations per minute of incorporated thymidine from triplicate wells was determined. The $IC_{50}$ (nM concentration required to inhibit 50% of the maximally observed incorporation of thymidine) for Compounds 9 and 10 of the present invention, and reference compounds ATRA and TTNBP are shown below in Tables 4, 5 and 6 for the cell lines RPMI 8226, ME 180 and AML-193 respectively.

Viability

Selected compounds of the present invention were also measured to determine their cytotoxicity on the above-identified cell lines. The procedure used was identical, with only slight modifications, to the assay described in T. Mosmann, "Rapid colorimetric assay for cellular growth and survival: application to proliferation and cytotoxicity assays", 65 J. Inmunol. Meth., 55 (1983), the disclosure of which is herein incorporated by reference. RPMI 8226 or AML-193 cells were plated in a 96 well round bottom microtiter plate (Costar) at a density of 1,000 cells/well. To appropriate wells, retinoid test compounds were added at the final concentrations indicated for a final volume of 150 µL/well. The plates were incubated for 96 hours at 37° C. in a humidified atmosphere of 5% $CO_2$ in air. Subsequently, 15 µL of a filter sterilized tetrazolium dye in phosphate buffered saline (Promega, Madison, Wis.) was added to each well and the cells were incubated for an additional four hours. Subsequent manipulations of the cultures were as described below.

ME 180 cells, harvested by trypsinization were plated in a 96 well flat bottom microtiter plate (Costar) at a density of 2,000 cells/well. The cultures were treated as described above for RPMI 8226.

After the four hours incubation, 100 µL of a solubilization/stop solution was added to each well (Promega, Madison, Wis.). The plates were allowed to stand overnight at 37° C. in the humidified atmosphere. The absorbance at 570–600 nm wavelength was recorded for each well using a Biomek ELISA plate reader (Beckman Instruments). The IC50 (nM concentration required to inhibit 50% of the mitochondrial function, and ultimately, the viability of the cells) for Compounds 9 and 10 of the present invention, and reference compounds ATRA and TTNBP are also shown below in Table 4, 5 and 6 for the cell lines RPMI 8226, ME 180 and AML-193 respectively.

Table 4: Inhibitory concentration required to inhibit 50% of the maximally observed radiolabeled thymidine (TdR $IC_{50}$) in nM, and inhibitory concentration required to inhibit 50% of the mitochondrial function (MTS $IC_{50}$) in nM, for Compounds 9 and 10, and reference compounds ATRA and TTNBP on the RPMI 8226 cell line.

| Compound | TdR $IC_{50}$ (nM) | MTS $IC_{50}$ (nM) |
| --- | --- | --- |
| 9 | 0.3 | 253 |
| 10 | 60 | 570 |
| ATRA | 102 | 756 |
| TTNPB | 0.2 | 10 |

Table 5: Inhibitory concentration required to inhibit 50% of the maximally observed radiolabeled thymidine (TdR $IC_{50}$) in nM, and inhibitory concentration required to inhibit 50% of the mitochondrial function (MTS $IC_{50}$) in nM, for Compounds 9 and 10, and reference compounds ATRA and TTNBP on the ME 180 cell line.

| Compound | TdR $IC_{50}$ (nM) | MTS $IC_{50}$ (nM) |
| --- | --- | --- |
| 9 | 0.1 | 1.3 |
| 10 | 62 | 370 |
| ATRA | 253 | 890 |
| TTNPB | 0.4 | 187 |

Table 6: Inhibitory concentration required to inhibit 50% of the maximally observed radiolabeled thymidine (TdR $IC_{50}$) in nM, and inhibitory concentration required to inhibit 50% of the mitochondrial function (MTS $IC_{50}$) in nM, for Compounds 9 and 10, and reference compounds ATRA and TTNBP on the AML-193 cell line.

| Compound | TdR $IC_{50}$ (nM) | MTS $IC_{50}$ (nM) |
| --- | --- | --- |
| 9 | 0.1 | 1000 |
| 10 | 0.01 | 1000 |
| ATRA | 197 | 1000 |
| TTNPB | 0.1 | 1000 |

EXAMPLE 27

The following examples provide illustrative pharmacological composition formulations: Hard gelatin capsules are prepared using the following ingredients:

| | Quantity (mg/capsule) |
| --- | --- |
| Compound 9 | 140 |
| Starch, dried | 100 |
| Magnesium stearate | 10 |
| Total | 250 mg |

The above ingredients are mixed and filled into hard gelatin capsules in 250 mg quantities. A tablet is prepared using the ingredients below:

| | Quantity (mg/tablet) |
| --- | --- |
| Compound 9 | 140 |
| Cellulose, microcrystalline | 200 |
| Silicon dioxide, fumed | 10 |
| Stearic acid | 10 |
| Total | 360 mg |

The components are blended and compressed to form tablets each weighing 360 mg . Tablets, each containing 60 mg of active ingredient, are made as follows:

| | Quantity (mg/tablet) |
|---|---|
| Compound 9 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, are then added to the granules which, after mixing, are compressed on a tablet machine to yield tablets each weighing 150 mg.

Suppositories, each containing 225 mg of active ingredient, may be made as follows:

| | |
|---|---|
| Compound 9 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

Compound 9 100 mg

Isotonic saline 1,000 ml

Glycerol 100 ml

The compound is dissolved in the glycerol and then the solution is slowly diluted with isotonic saline. The solution of the above ingredients is then administered intravenously at a rate of 1 ml per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A compound of the formulae:

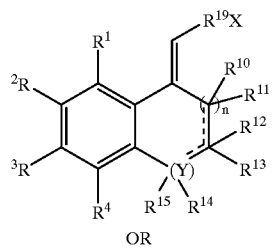

(II)

OR

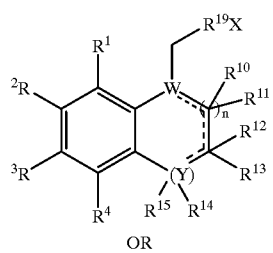

(III)

OR

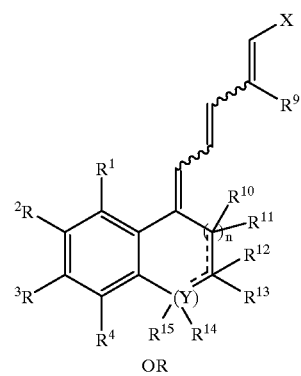

(IV)

OR

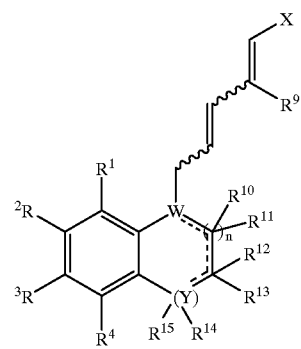

(V)

wherein:

$R^1$, $R^2$ and $R^4$ each independently are hydrogen, aryl, heteroaryl, $CF_3$ or a $C_2$–$C_6$ alkyl, fluoroalkyl or perfluoroalkyl optionally substituted with $^{14}CH_3$, $^{13}CH_3$, $CD_3$, $C^3H_3$, and/or $^{13}CD_3$;

$R^3$ is each independently are hydrogen, $CF_3$, a $C_1$–$C_3$ alkyl, a $C_1$ to $C_3$ fluoroalkyl or perfluoroalkyl, or $OR^6$, where $R^6$ is hydrogen, $CF_3$, a $C_1$–$C_2$ alkyl or a $C_1$ to $C_2$ fluoroalkyl or perfluoroalkyl, provided, however, that $R^1$ cannot be $CF_3$ or alkyl, fluoroalkyl or perfluoroalkyl when $R^3$ is $CF_3$ or alkyl, fluoroalkyl or perfluoroalkyl;

$R^9$ is a $C_1$–$C_4$ alkyl;

$R^{10}$ through $R^{15}$ each independently are hydrogen, a $C_1$–$C_6$ alkyl or $CF_3$;

X is $COOR^{16}$, $CONHR^{17}$, or $CONR^{17}R^{18}$ where $R^{16}$ represents hydrogen or a $C_1$–$C_6$ alkyl, and where $R^{17}$ and $R^{18}$ each independently represent a $C_1$–$C_6$ alkyl, or an aryl or heteroaryl optionally substituted with OH, F, Br, Cl or I, provided, however, that $R^{17}$ and $R^{18}$ both cannot be an aryl or heteroaryl;

Y is C, O, S or N, provided that, when Y is O, then $R^{14}$ and $R^{15}$ do not exist, and when Y is N, then $R^{14}$ and $R^{15}$ cannot be $CF_3$, and when Y is S, then $R^{14}$ and $R^{15}$ can independently or together represent O, or may be absent altogether;

W is N or $CR^{16}$, where $R^{16}$ has the same definition given above;

$R^{19}$ is an aryl or heteroaryl optionally substituted with one or more substituents selected from the group consisting of hydrogen, F, Cl, Br, I or a $C_1$–$C_6$ alkyl, wherein X has the same definition given above;

n is 0, 1 or 2;

the dotted lines designate optional double bonds; and the wavy lines depict carbon to carbon bonds in either the cis or trans configurations, provided, however, that when $R^1$, $R^2$ and $R^4$ are all hydrogen, then $R^3$ cannot be aryl.

2. A compound according to claim 1, wherein $R^1$, $R^2$ and $R^4$ independently represent $C_3$–$C_6$ branched alkyls, fluoroalkyls or perfluoroalkyls.

3. A compound according to claim 1, wherein $R^2$ and $R^4$ independently represent $C_3$–$C_6$ branched alkyls, fluoroalkyls or perfluoroalkyls, and $R^1$ and $R^3$ are all hydrogen.

4. A compound according to claim 1, wherein $R^2$ and $R^4$ independently represent isopropyl, t-butyl or $CF_3$, and $R^1$ and $R^3$ are all hydrogen.

5. A compound according to claim 1, selected from the group consisting of ethyl (2E,4E,6E)-6-(6,8,-di-t-butylchroman-4-ylidene)-3-methylhexa-2,4,6-trienoate; ethyl (2E,4E,6Z)-6-(6,8,-di-t-butylchroman-4-ylidene)-3-methylhexa-2,4,6-trienoate; (2E,4E,6E)-6-(6,8,-di-t-butylchroman-4-ylidene)-3-methylhexa-2,4,6-trienoic acid; and (2E,4E,6Z)-6-(6,8,-di-t-butylchroman-4-ylidene)-3-methylhexa-2,4,6-trienoic acid.

6. A compound according to claim 1, wherein the compound comprises a retinoid compound.

7. A compound according to claim 6, wherein in a co-transfection assay the compound has an $EC_{50}$ of less than 100 nM on one or more retinoid receptors.

8. A compound according to claim 6, wherein in a co-transfection assay the compound has an $EC_{50}$ of less than 50 nM on one or more retinoid receptors.

9. A compound according to claim 6, wherein in a co-transfection assay the compound has an $EC_{50}$ of less than 20 nM on one or more retinoid receptors.

10. A compound according to claim 6, wherein in a co-transfection assay the compound has an $EC_{50}$ of less than 10 nM on one or more retinoid receptors.

11. A compound according to claim 6, wherein in a co-transfection assay the compound is a selective RAR agonist.

12. A compound according to claim 11, wherein in a co-transfection assay the compound is at least two times more potent an activator of RAR than of RXR.

13. A compound according to claim 11, wherein in a co-transfection assay the compound is at least five times more potent an activator of RAR than of RXR.

14. A compound according to claim 11, wherein in a co-transfection assay the compound is at least ten times more potent an activator of RAR than of RXR.

15. A compound according to claim 11, wherein in a co-transfection assay the compound is at least one hundred times more potent an activator of RAR than of RXR.

16. A compound according to claim 6, wherein in a co-transfection assay the compound is a selective RXR agonist.

17. A compound according to claim 16, wherein in a co-transfection assay the compound is at least two times more potent an activator of RXR than of RAR.

18. A compound according to claim 16, wherein in a co-transfection assay the compound is at least five times more potent an activator of RAR than of RXR.

19. A compound according to claim 16, wherein in a co-transfection assay the compound is at least ten times more potent an activator of RAR than of RXR.

20. A compound according to claim 16, wherein in a co-transfection assay the compound is at least one hundred times more potent an activator of RAR than of RXR.

21. A compound according to claim 6, wherein in a co-transfection assay the compound is an activator of both RAR and RXR.

22. A compound according to claim 1, wherein the compound is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

23. A pharmaceutical composition comprising a compound of claim 1 and a pharmaceutically acceptable carrier.

24. A pharmaceutical composition according to claim 23, wherein the composition is formulated for oral, topical, intravenous, suppository or parental administration.

25. A pharmaceutical composition according to claim 23, wherein the compound is administered to a patient as a dosage unit at from about 10 µg/kg of body weight to about 500 mg/kg of body weight.

26. A pharmaceutical composition according to claim 23, wherein the compound is administered to a patient as a dosage unit at from about 10 µg/kg of body weight to about 250 mg/kg of body weight.

27. A pharmaceutical composition according to claim 23, wherein the compound is administered to a patient as a dosage unit at from about 20 µg/kg of body weight to about 100 mg/kg of body weight.

28. A pharmaceutical composition according to claim 23, wherein the composition is effective in treating skin-related diseases and conditions, cancerous and pre-cancerous conditions, diseases of the eye, cardiovascular diseases, inflammatory diseases, neurodegenerative diseases, diseases involving modulation of apoptosis, disease,, of the immune system, improper pituitary function, diseases involving human papilloma virus, wound healing or restoration of hair growth.

29. A method of affecting RAR and/or RXR activity comprising the in vivo administration of a compound according to claim 1.

30. A method of modulating processes mediated by RAR and/or RXR receptors comprising administering to a patient an effective amount of a compound according to claim 6.

31. A method of treating a patient requiring retinoid therapy comprising administering to the patient a pharmaceutically effective amount of a compound according to claim 6.

32. A method of treating a patient according to claim 31 wherein the compound is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

33. A method of treating a patient requiring retinoid therapy comprising administering to the patient a pharmaceutically effective amount of a pharmaceutical composition according to claim 23.

34. A method of treating a patient according to claim 33, wherein the composition is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

35. A method for determining the presence of one or more RAR and/or RXR receptors in a sample comprising combining a compound according to claim 1 with a sample containing one or more unknown retinoid receptors, and determining whether said compound binds to a receptor in the sample.

36. A ligand-retinoid receptor complex formed by the binding of a compound according to claim 1 to a RAR and/or RXR receptor.

37. A method of purifying retinoid receptors comprising combining a compound according to claim 1 with a sample containing RAR and/or RXR receptors, allowing said compound to bind said receptors, and separating out the bound combination of said compound and said RAR and/or RXR receptors.

* * * * *